(12) United States Patent
Russo et al.

(10) Patent No.: US 12,022,994 B2
(45) Date of Patent: Jul. 2, 2024

(54) SOFT ACTUATORS FOR POP-UP LAMINATE STRUCTURES

(71) Applicant: President and Fellows of Harvard College, Cambridge, MA (US)

(72) Inventors: Sheila Russo, Cambridge, MA (US); Tommaso Ranzani, Cambridge, MA (US); Robert Wood, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 841 days.

(21) Appl. No.: 16/301,798

(22) PCT Filed: May 16, 2017

(86) PCT No.: PCT/US2017/032823
§ 371 (c)(1),
(2) Date: Nov. 15, 2018

(87) PCT Pub. No.: WO2017/200991
PCT Pub. Date: Nov. 23, 2017

(65) Prior Publication Data
US 2020/0315429 A1    Oct. 8, 2020

Related U.S. Application Data

(60) Provisional application No. 62/354,023, filed on Jun. 23, 2016, provisional application No. 62/336,874, filed on May 16, 2016.

(51) Int. Cl.
*A61B 1/00*    (2006.01)
*A61B 1/008*    (2006.01)
(Continued)

(52) U.S. Cl.
CPC .......... *A61B 1/00087* (2013.01); *A61B 1/008* (2013.01); *A61B 34/30* (2016.02);
(Continued)

(58) Field of Classification Search
CPC ..... A61B 1/00087; A61B 1/008; A61B 34/30; A61B 34/76; A61B 2034/301; B25J 9/142; B25J 15/0616; B25J 18/06
See application file for complete search history.

(56) References Cited

U.S. PATENT DOCUMENTS 8,835,666 B2    9/2014    Brazdil, Jr. et al.
2006/0028041 A1*  2/2006   Ono .................. B25J 15/10
                                                     294/119.3
(Continued)

FOREIGN PATENT DOCUMENTS

WO    WO-2013148340 A2 *   10/2013   .......... A47L 9/2836
WO    2014/147556 A1       9/2014
WO    2017/040733 A1       3/2017

OTHER PUBLICATIONS

S. Konishi, "Small, soft and safe micro-machines for biomedical applications," 2015 Transducers—2015 18th International Conference on Solid-State Sensors, Actuators and Microsystems (Transducers), Anchorage, AK, 863-866 (2015).
(Continued)

*Primary Examiner* — Anh Tuan T Nguyen
*Assistant Examiner* — Rynae E Boler
(74) *Attorney, Agent, or Firm* — Modern Times Legal; Robert J. Sayre

(57) ABSTRACT

A laminate linkage with soft actuation includes a plurality of rigid plates joined at flexible joints; at least one balloon bonded to at least one of the rigid plates and configured to generate a displacement (extension, a change of yaw, and/or a change of pitch) of at least one of the rigid plates; and a
(Continued)

fluid source in fluid communication with an interior volume of the balloon and configured to pump fluid into the balloon to generate the displacement of at least one of the rigid plates.

10 Claims, 17 Drawing Sheets

(51) Int. Cl.
*A61B 34/00* (2016.01)
*A61B 34/30* (2016.01)
*B25J 9/14* (2006.01)
*B25J 15/06* (2006.01)
*B25J 18/06* (2006.01)

(52) U.S. Cl.
CPC ............... *A61B 34/76* (2016.02); *B25J 9/142* (2013.01); *B25J 15/0616* (2013.01); *B25J 18/06* (2013.01); *A61B 2034/301* (2016.02)

(56) References Cited

U.S. PATENT DOCUMENTS

| | | | |
|---|---|---|---|
| 2013/0106127 A1* | 5/2013 | Lipson | B25J 15/0023 294/189 |
| 2014/0109560 A1* | 4/2014 | Ilievski | B25J 9/142 60/327 |
| 2015/0090113 A1* | 4/2015 | Galloway | B25J 9/142 92/48 |
| 2015/0257839 A1* | 9/2015 | Vause | B25J 15/12 606/130 |
| 2016/0184041 A1* | 6/2016 | Gafford | H05K 1/18 606/174 |

OTHER PUBLICATIONS

S. Konishi, "Small soft safe micromachines for biomedical applications," 2014 IEEE International Electron Devices Meeting, San Francisco, CA, 31.6.1-31.6.4 (2014).

S. Konishi, "Small, soft, safe micromachine for minimally invasive surgery," 2011 International Meeting for Future of Electron Devices, Osaka, 20-21 (2011).

D. Qin, et al., "Soft lithography for micro- and nanoscale patterning," 5 Nature Protocols 491-502 (2010).

S. Russo, et al., "A soft pop-up proprioceptive actuator for minimally invasive surgery," The Hamlyn Symposium on Medical Robotics (2016).

S. Russo, et al., "Soft pop-up mechanisms for micro surgical tools: design and characterization of compliant millimeter-scale articulated structures," 2016 IEEE International Conference on Robotics and Automation (ICRA), Stockholm, 750-757 (2016).

K. Ikuta, et al. "Safety active catheter with multi-segments driven by innovative hydro-pressure micro actuators," The Sixteenth Annual International Conference on Micro Electro Mechanical Systems, IEEE, Kyoto, Japan, 130-135 (2003).

T. Ranzani, et al., "A bioinspired soft manipulator for minimally invasive surgery," 10 Bionspir. Biomim. 035008 (2015).

M. Cianchetti, et al., "Soft Robotics Technologies to Address Shortcomings in Today's Minimally Invasive Surgery: The STIFF-FLOP Approach," 1 Soft Robotics 122-131 (2014).

J. P. Whitney, et al., "Pop-up book MEMS," 21 J. Micromech. Microeng. 1-7 (2011).

P. Swaney, et al., "Tendons, Concentric Tubes, and a Bevel Tip: Three Steerable Robots in One Transoral Lung Access System," IEEE Int. Conf. Robot Autom., May 2015, 5378-5383 (2015).

R. Hendrick, et al., "Hand-held transendoscopic robotic manipulators: A transurethral laser prostate surgery case study," 34 Int. J. Rob. Res. 1559-1572 (2015).

S. Russo, et al. "An additive millimeter-scale fabrication method for soft bio-compatible actuators and sensors,".

* cited by examiner

SOFT ACTUATORS FOR POP-UP LAMINATE STRUCTURES

This application is a continuation of U.S. application Ser. No. 14/909,792 (now U.S. Pat. No. 10,376,326 B2, issued 13 Aug. 2019), which is a national-phase entry of PCT/US2014/049588, filed 4 Aug. 2014. This application also claims the benefit of U.S. Provisional Application No. 61/862,066, filed 4 Aug. 2013. The entire contents of these earlier applications are incorporated herein by reference.

GOVERNMENT SUPPORT

This invention was made with government support under Grant No. FA8650-15-C-7548 awarded by the Defense Advanced Research Projects Agency. The U.S. Government has certain rights in the invention.

BACKGROUND

The drive towards early detection of cancer and minimally invasive surgery (MIS) motivates the research in the development of miniaturized smart instruments to perform treatment with minimal access trauma. The fabrication of articulated structures, able to effectively perform tasks in complex and highly unstructured environments such as the human body, presents several challenges mainly due to the lack of viable manufacturing techniques and actuation strategies at these scales. Instruments need to provide the surgeon with sensory feedback as well as dexterity and forces necessary at the surgical site, especially when flexible endoscopes are used to reach the target area, such as in natural orifice transluminal endoscopic surgery (NOTES).

Several robotic systems as well flexible endoscopic multitask platforms have been proposed to overcome limitations of current instruments and to provide better and more sophisticated devices to surgeons. When dealing with endoscopic procedures, however, current devices still suffer from limited maneuverability and manipulation capabilities and a lack of integrated sensing, which limit their potential use to perform advanced endoluminal surgery. Additional solutions include integrating robotic arms or manipulation aids directly on the tip of an endoscope.

This strategy allows increasing dexterity and instrument triangulation (deflecting the instruments from the vision system) without losing flexibility of the endoscope in reaching the target. These solutions, however, introduce technical challenges—in particular, proximal actuation typically requires cables along the endoscope, resulting in cable friction and backlash, which can affect accuracy, controllability and, thus, the intuitiveness of the system. Distal actuation approaches still lack viable technologies due to challenges regarding scalability and safety of the materials, currents, and voltages needed. A promising approach has been proposed by Webster, et al., wherein active cannulas are used in combination with conventional endoscopes for transurethral prostate surgery and transoral lung surgery [R. J. Hendrick, et al., "Hand-held transendoscopic robotic manipulators: A transurethral laser prostate surgery case study," The International Journal of Robotics Research 0278364915585397 (2015), and P. J. Swaney, et al., "Tendons, concentric tubes, and a bevel tip: Three steerable robots in one transoral lung access system," Robotics and Automation (ICRA), 2015 IEEE International Conference on. IEEE 5378-5383 (2015)]. Recent studies have focused on increasing the amount of articulation achievable at the instrument tip, as well as integrating sensing capabilities for these systems.

The pop-up MEMS manufacturing paradigm creates three-dimensional microstructures and devices, based on the folding of multilayer rigid-flex laminates [J. Whitney, et al., "Pop-up book mems," 21 Journal of Micromechanics and Microengineering 115021 (2011)]. This method enables fabrication of highly complex structures with embedded actuation and sensing, and it has been successfully applied in fabricating functional bioinspired robots as well as mechanisms and sensors for surgical applications. Advantages of this approach include batch manufacturing (low cost) and flexibility in the material selection.

Soft technologies have recently been proposed for medical devices [M. Cianchetti, et al., "Soft robotics technologies to address shortcomings in today's minimally invasive surgery: The stiff-flop approach," 1 Soft Robotic 122-131 (June 2014) and T. Ranzani, et al., "A bioinspired soft manipulator for minimally invasive surgery," 10 Bioinspiration & Biomimetics 035008 (2015)]. Soft micro-actuators for medical applications have also been proposed in [K. Ikuta, et al., "Safety active catheter with multi-segments driven by innovative hydro-pressure micro actuators," MEMS-03 Kyoto, IEEE, The Sixteenth Annual International Conference on Micro Electro Mechanical Systems 130-135 (2003), and S. Konishi, "Small soft safe micromachines for biomedical applications," Electron Devices Meeting (IEDM), 2014 IEEE International 31.6.1-31.6.4 (2014)]. However, fine control and sensor integration on fully soft systems present several challenges that currently limit their potential in microsurgical applications, and the achievable forces with such actuators are limited to the mN range.

SUMMARY

Methods and apparatus for soft actuation of laminate structures are described herein, where various embodiments of the apparatus and methods may include some or all of the elements, features and steps described below.

A laminate linkage with soft actuation comprises a plurality of rigid plates joined at flexible joints; at least one balloon bonded to at least one of the rigid plates and configured to generate a displacement of at least one of the rigid plates selected from extension, a change of yaw, a change of pitch, and combinations thereof; and a fluid source (e.g., a hydraulic or pneumatic pump) configured to pump fluid (e.g., liquid or gas) into the balloon to generate the displacement of at least one rigid plate.

A plurality of the balloons can be respectively joined to different rigid plates, and different balloons can be configured (in relation to the rigid plates) to generate different types of displacement. In particular, respective balloons and rigid plates can be configured to respectively generate extension, change of yaw, and change of pitch of rigid plates.

The balloons and rigid plates can be laminated together, and lamination can be achieved via ultrasonic bonding; in other embodiments, lamination can be achieved via plasma bonding, adhesive bonding, or thermoforming. In additional embodiments, the rigid plates and balloons can be optically transparent. The balloons can be formed of a mixture of PDMS and silicone rubber; and the balloons can be mounted externally or internally to joints. The dimensions of the laminate linkage can range from 1-5 mm.

In a particular embodiment, the laminate linkage is mounted on an endoscope or other flexible instrument (such as a catheter). In additional embodiments, sensors can be mounted along the linkage to detect contact forces or for determining position (e.g., from in-vivo contact with tissue).

In additional embodiments, the rigid plates can be electrically conductive or include electrodes to form capacitive sensors. Additionally, electromagnetic shielding can be embedded in the structure to prevent interferences. In still more embodiments, outer surfaces of the laminate linkage are all formed of biocompatible material (e.g., silicone elastomer).

Described herein is a manufacturing technique that enables the integration of soft materials and soft fluidic micro-actuators in the pop-up MEMS paradigm. Such a technique represents a promising approach to the design and fabrication of low-cost and scalable articulated mechanisms provided with sensing capabilities and on-board actuation with potential applications in the field of minimally invasive surgery. Design and integration of soft components in the rigid-flex laminates is described along with the resulting soft pop-up mechanisms realized at different scales. Prototype characterization is presented, demonstrating forces and dexterity in a range suitable for surgical applications, as well as being suited for the integration of sensing capabilities. Based on these results, a multi-articulated robotic arm has been fabricated and mounted on top of an endoscope model to provide a proof of concept of simple robotic mechanisms that can be useful in a surgical scenario.

Introducing rigid structures into soft robots can potentially lead to several advantages—e.g., they can constrain motions in desired directions, thus increasing controllability and reliability of the system. In particular embodiments, multiple hybrid soft pop-up actuators are combined into a multi-articulated robotic arm that is integrated with current flexible endoscopes to improve distal dexterity and enable tissue retraction. The provision of compliant and flexible materials in the actuators allows for their safe interaction with biological tissue. Furthermore, while the low elastic modulus of soft materials can limit the interaction forces between the robots and a surgical target, stiffening mechanisms (e.g., rigid components) can be incorporated into the device to enhance the transfer of forces between the device and biological tissue.

In particular embodiments, the laminate structure can be made exclusively of biocompatible materials to prevent adverse interactions between biological tissue and the laminate structure. The use of soft actuators also promotes safe interaction with biological tissue, as there is no need for high voltages or temperatures required by other types of actuators. Further still, fabrication of the laminate structure can be readily scaled by producing a plurality of the devices from a single, large laminate and cutting the devices from the large laminate after fabrication. Use of the laminate fabrication technique also allows for monolithic integration of the fluid lines for actuation and conductive traces for capacitive sensing without a need for manual intervention to assemble discrete components, while promoting placement accuracy of components, thus enabling scalability and nearly arbitrary design complexity.

The laminate structure can accordingly augment the therapeutic capabilities of flexible endoscopic instruments [such as a CF-100L flexible endoscopic (13.3 mm in outer diameter) from Olympus Corp. of Tokyo, Japan]. Adding a laminate linkage arm, as described herein, can increase the endoscope diameter by only 1.8 mm. Small-scale, distally actuated mechanisms can enable endoluminal manipulation tasks in endoscopic surgery, e.g., providing the necessary counter-traction for safe en bloc resection of neoplasms in the gastrointestinal tract.

Where the laminate structure is in the form of a bending actuator, the bending actuator can follow a trajectory of a regular circumference arc when actuated, whereas a typical bending fully soft actuator tends to roll around itself in a trajectory with a shrinking radius.

BRIEF DESCRIPTION OF THE DRAWINGS

FIG. 4 shows fabrication of actuators via a SU-8 patterned silicon wafer. FIG. 5 shows fabrication of a composite layer by bonding the soft patterned layer onto a hard material modified by silanization. FIG. 6 shows integration of the composite layer in the lamination process. FIG. 7 show final release of the mechanisms and soft fluidic actuation.

FIG. 8 is a linear actuator based on a Sarrus linkage mechanism integrating a soft fluidic micro-actuator in the center. FIG. 9 is a bending mechanism based on the same Sarrus linkage mechanism of FIG. 8. FIG. 10 is a second bending mechanism based on a series of rigid links with an external soft fluidic micro-actuator. FIG. 11 is a schematic illustration of the model used to describe FIGS. 8 and 9. FIG. 12 is a schematic illustration of the model used to describe FIG. 10

The dashed line represents the output from the model. Meanwhile, the solid lines represent the mean value; and the shaded area represents one standard deviation computed on two prototypes for each size, tested three times each.

Figure 18:
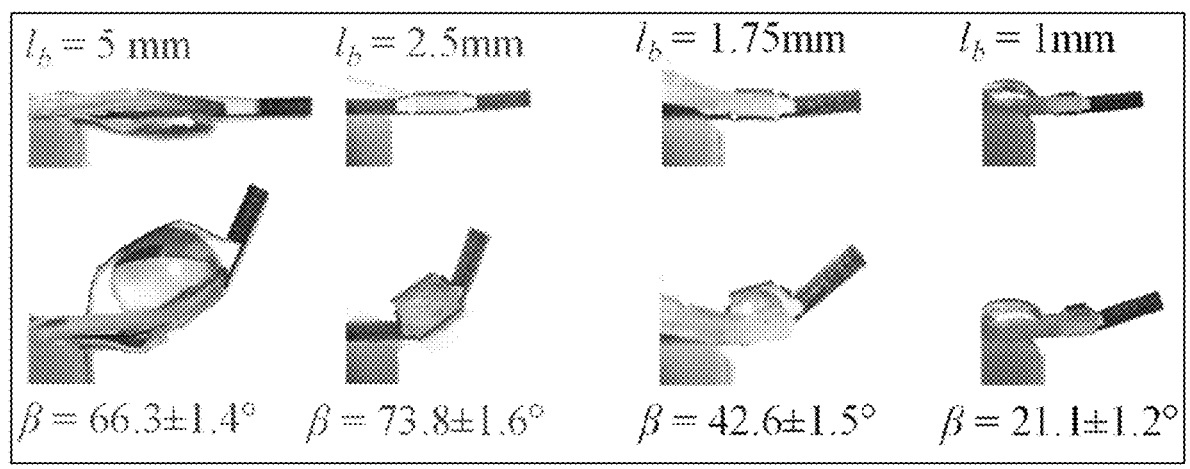

FIG. 18 includes photographs showing the IMJ prototypes at different $l_b$ dimensions at minimum (top) and maximum (bottom) bending angles.

Figure 19:
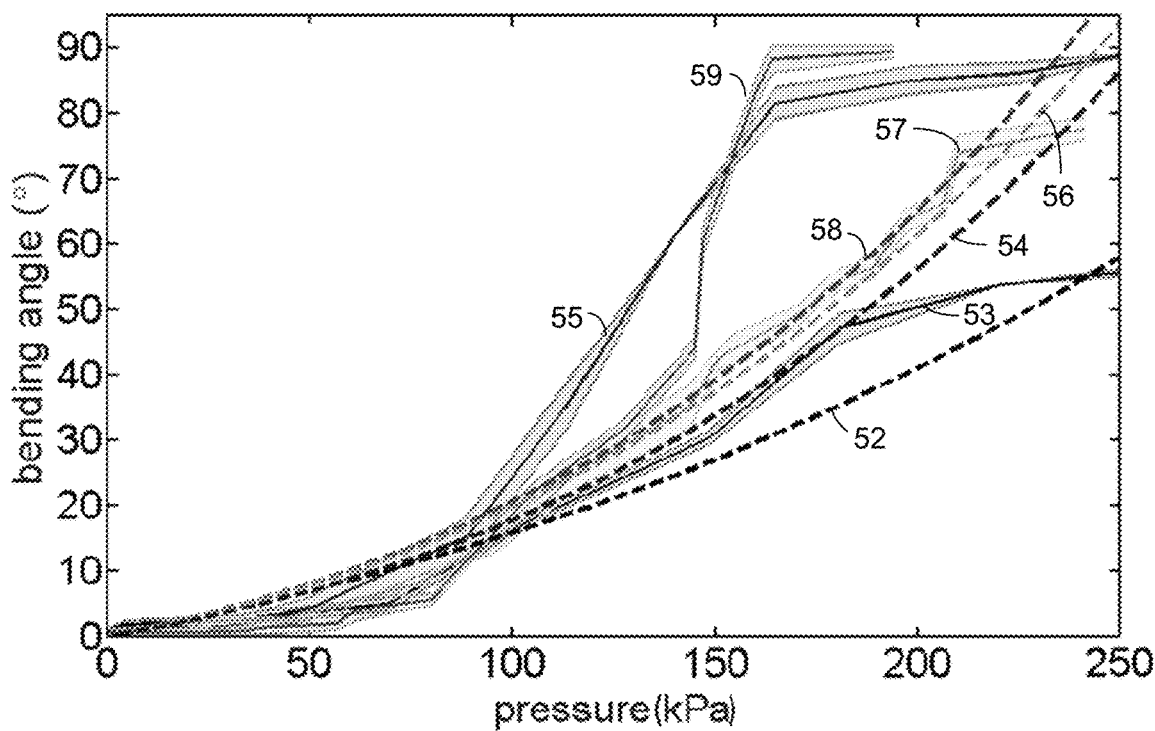

FIG. 19 plots the results of a bending angle characterization test for EMJ prototypes fabricated at different scales ($l_b$). The dashed line represents the output from the model. The solid line is the mean value, and the shaded area represents one standard deviation computed on two prototypes for each size, tested three times each.

Figure 20:
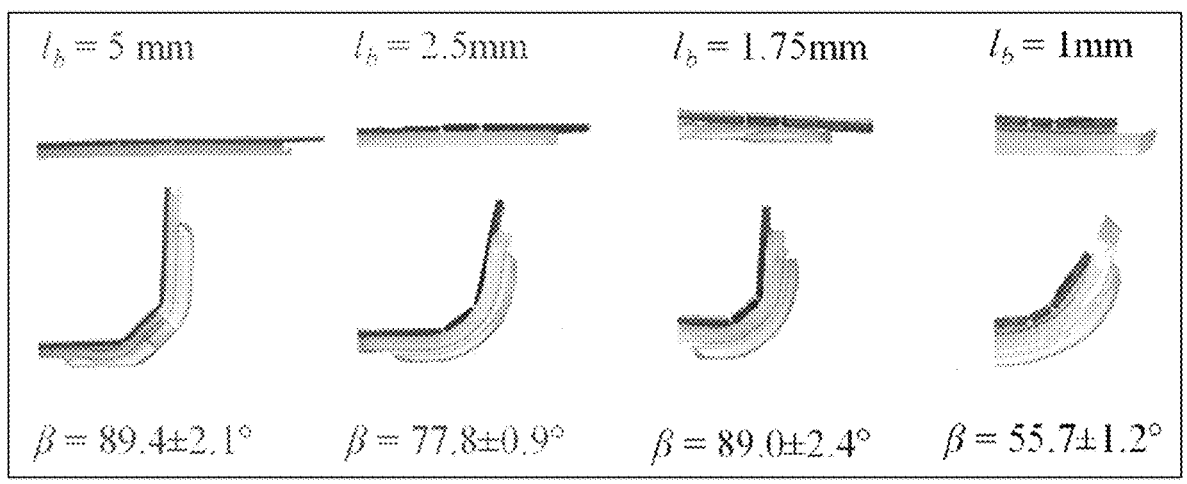

FIG. 20 includes photographs showing all of the EMJ prototypes at different $l_b$ at minimum (top) and maximum (bottom) bending angles.

Figure 21:
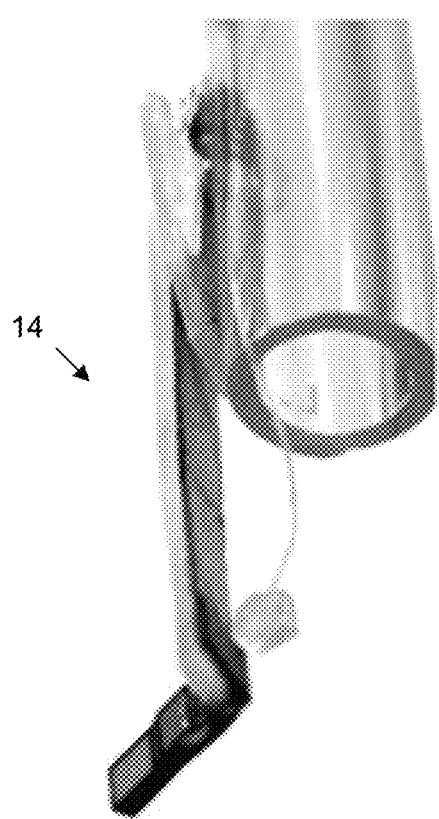
Figure 22:
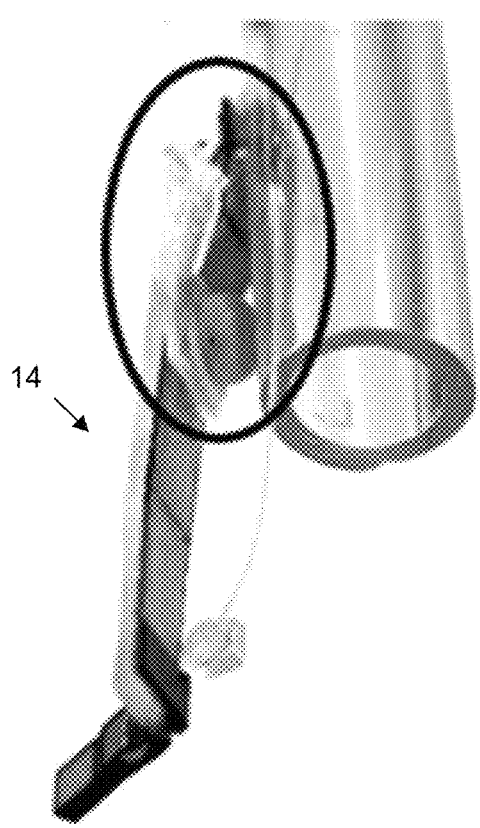
Figure 23:
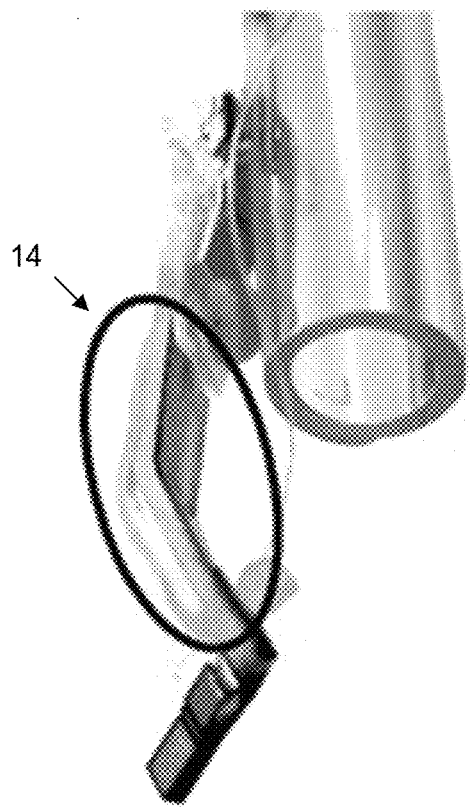
Figure 24:
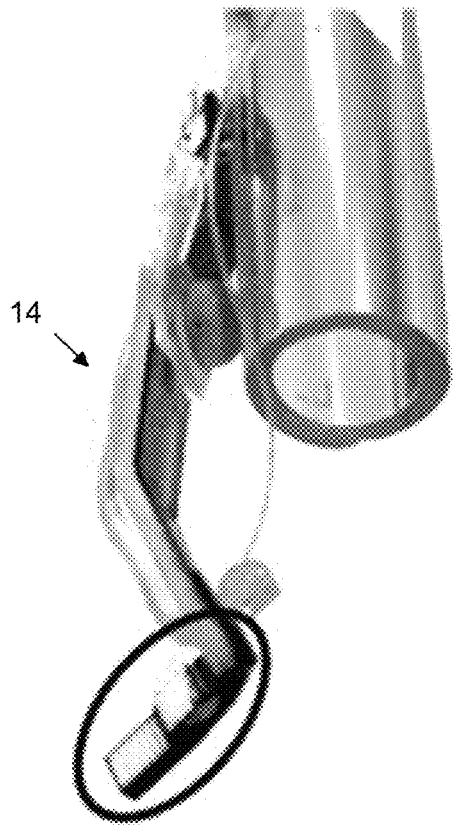

FIGS. 21-24 show a multi-articulated robotic arm. FIGS. 21 and 22 show expansion of the soft pop-up parallel mechanism to perform triangulation. FIG. 23 shows the yaw DOF (circled), while FIG. 24 shows the pitch DOF (circled).

Figure 25:
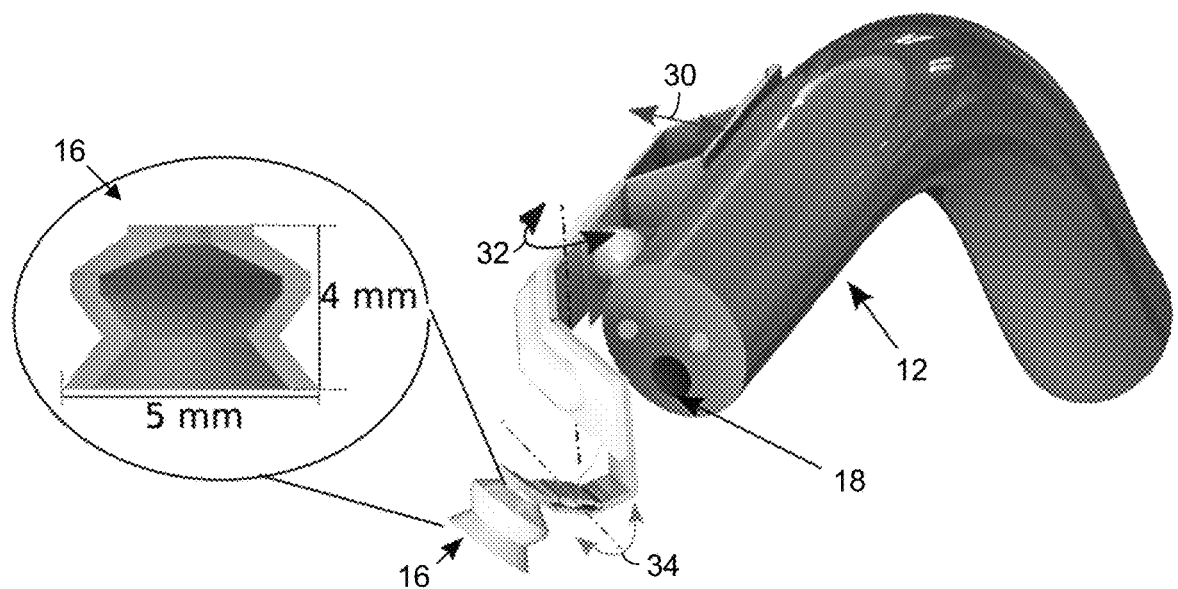
Figure 26:
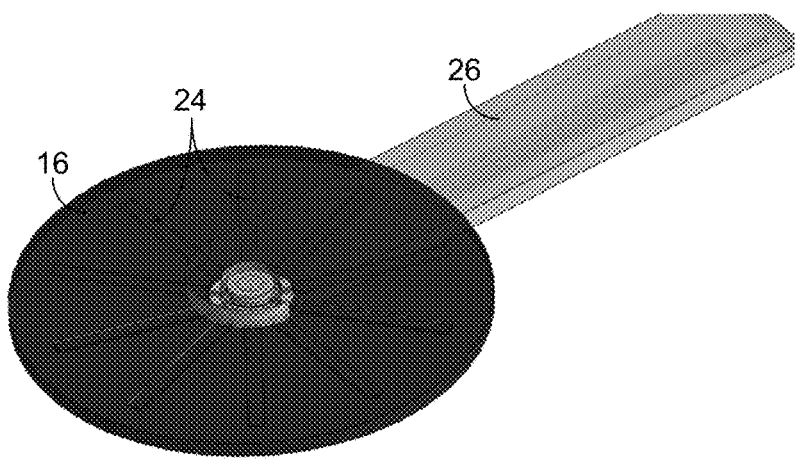
Figure 27:
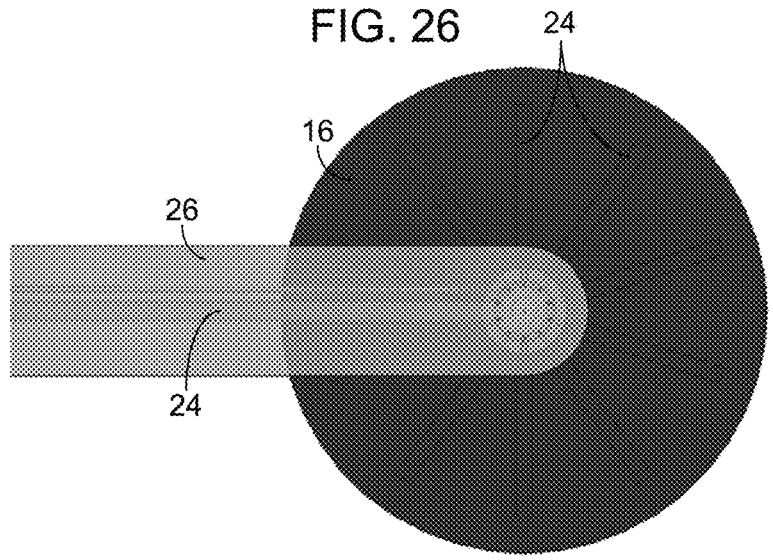
Figure 28:
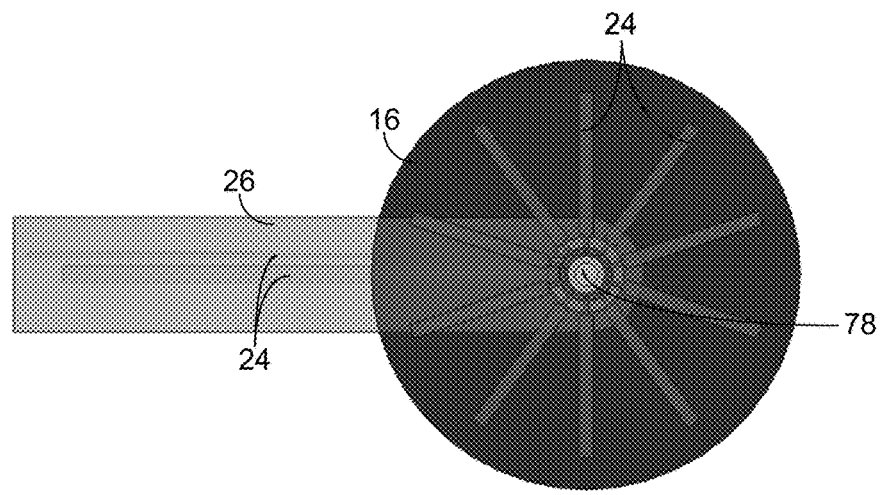

FIG. 25 is a CAD rendering of a soft pop-up arm with an integrated suction-based soft gripper.

FIGS. 26-29 respectively show a perspective view, a top view, a bottom view and a sectional side view of a laminate gripper structure.

Figure 30:
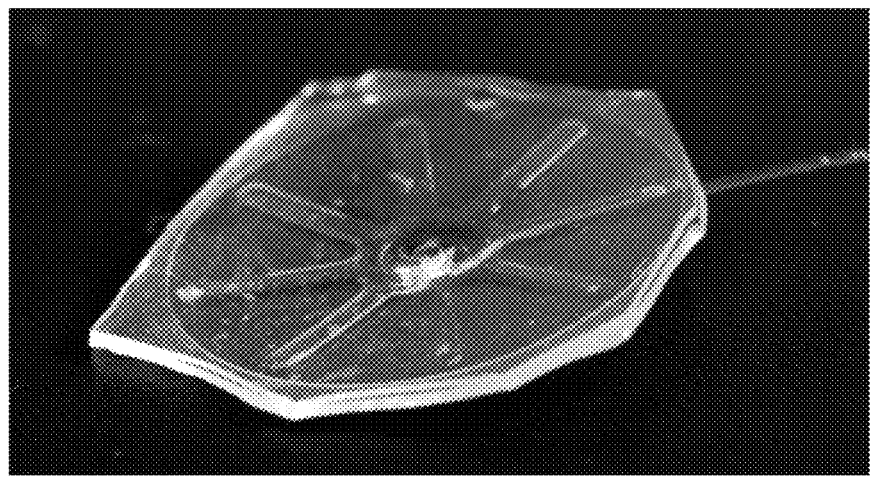

FIG. 30 is a photographic image of a laminate soft gripper in its flat, unactuated configuration.

Figure 31:
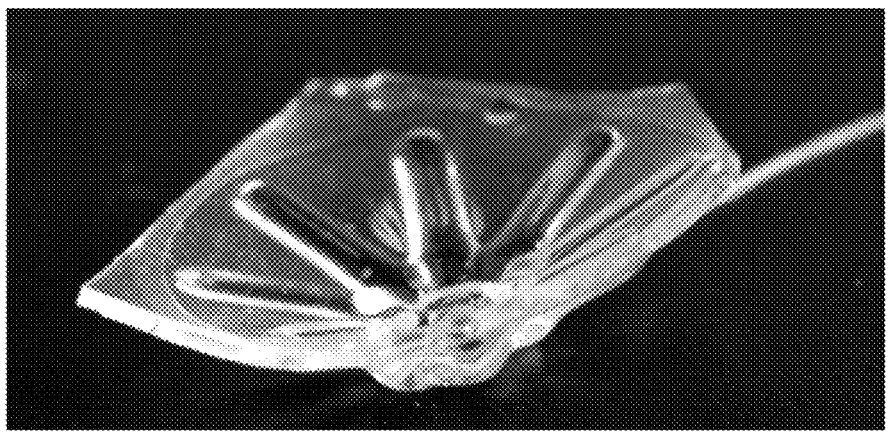

FIG. 31 is a photographic image of the laminate soft gripper of FIG. 30 with its internal channels pressurized to produce a concave dish structure.

Figure 32:
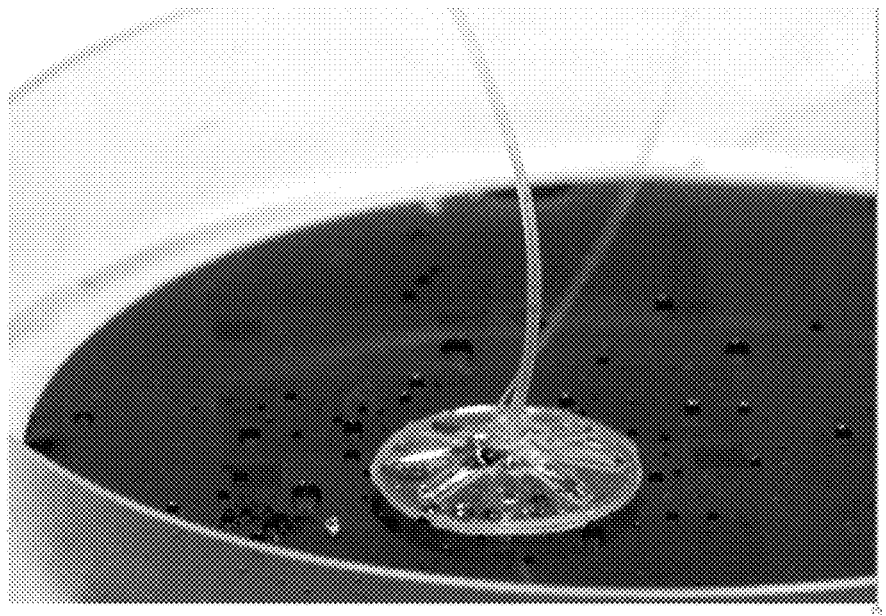

FIG. 32 is a photographic image of the soft gripper of FIG. 30 with its internal channels pressure actuated to press its outer edges against the surface.

Figure 33:
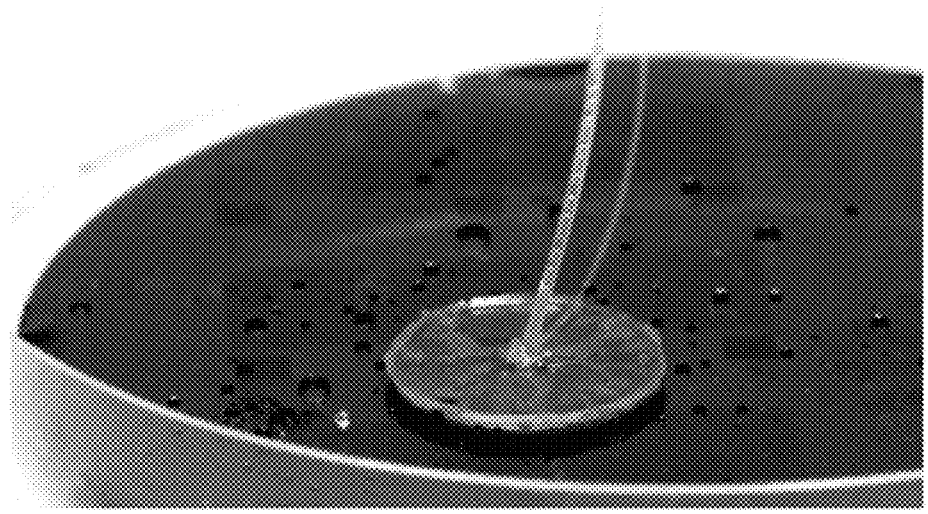

FIG. 33 is a photographic image of the soft gripper of FIG. 30 with a vacuum pressure applied through the piping and through a central orifice to remove the air from the dome of the soft gripper to adhere the entire surface of the contacting face of the soft gripper against the surface.

Figure 34:
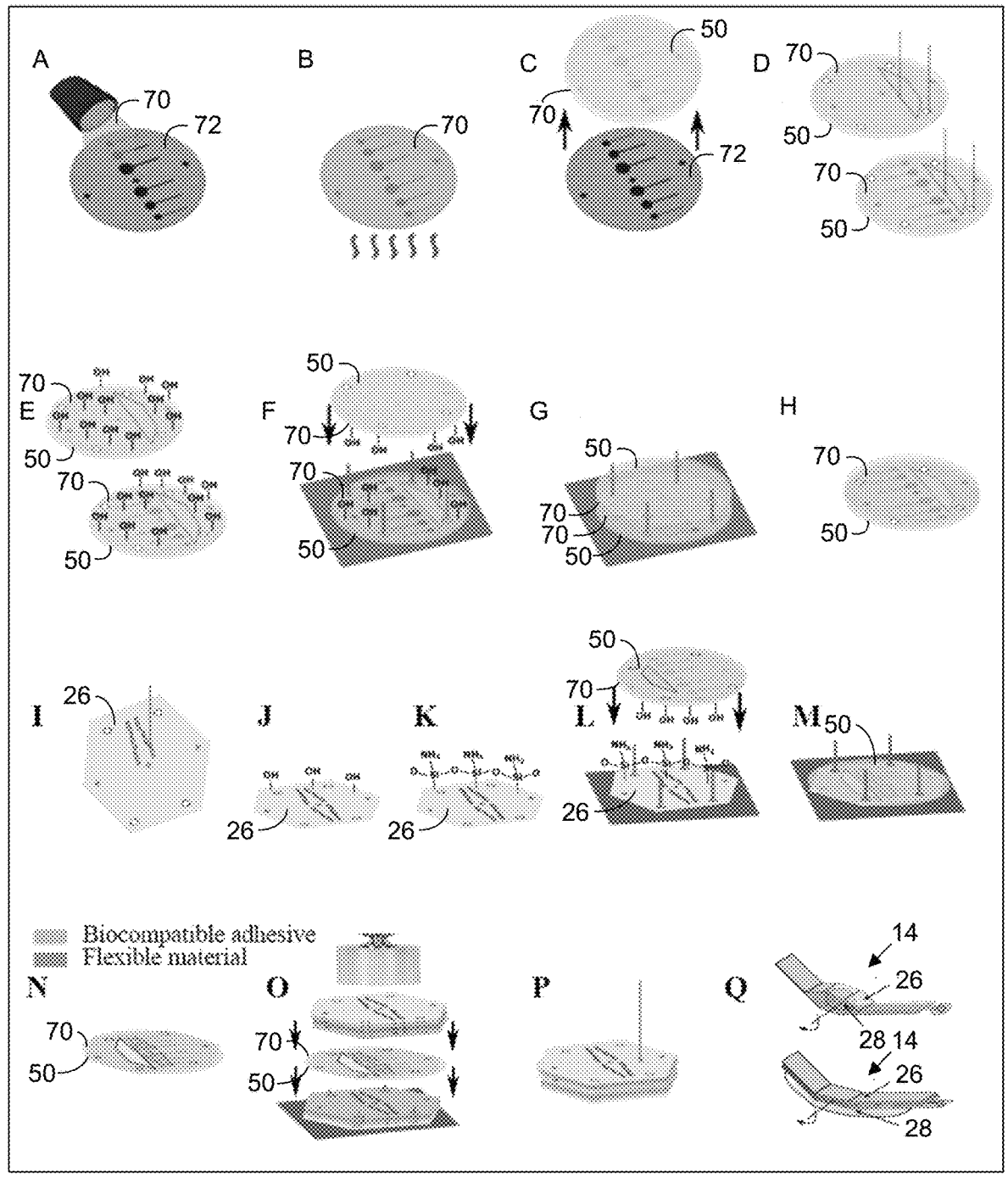

FIG. 34 illustrate steps in a process for fabricating a laminate linkage.

Figure 35:
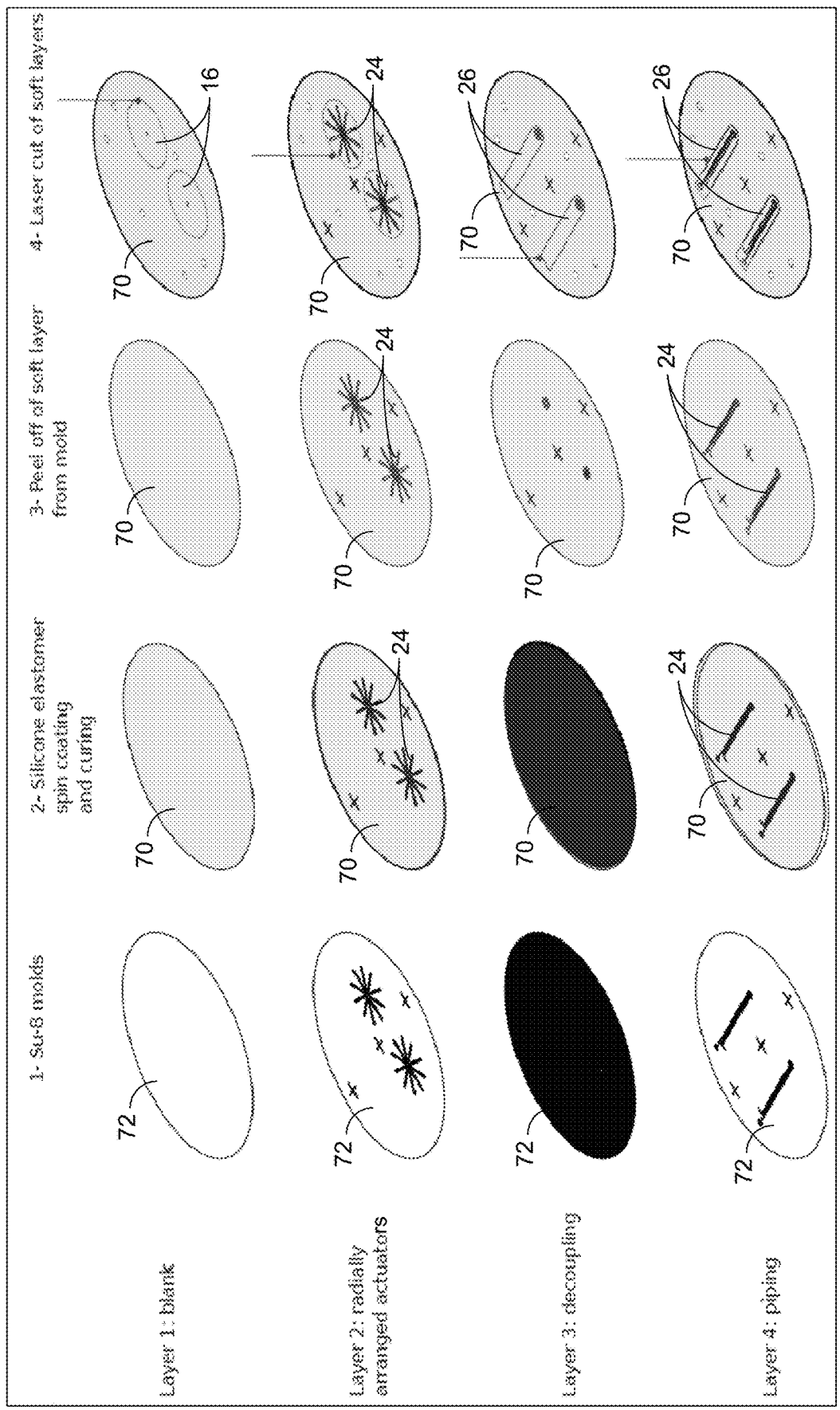
Figure 36:
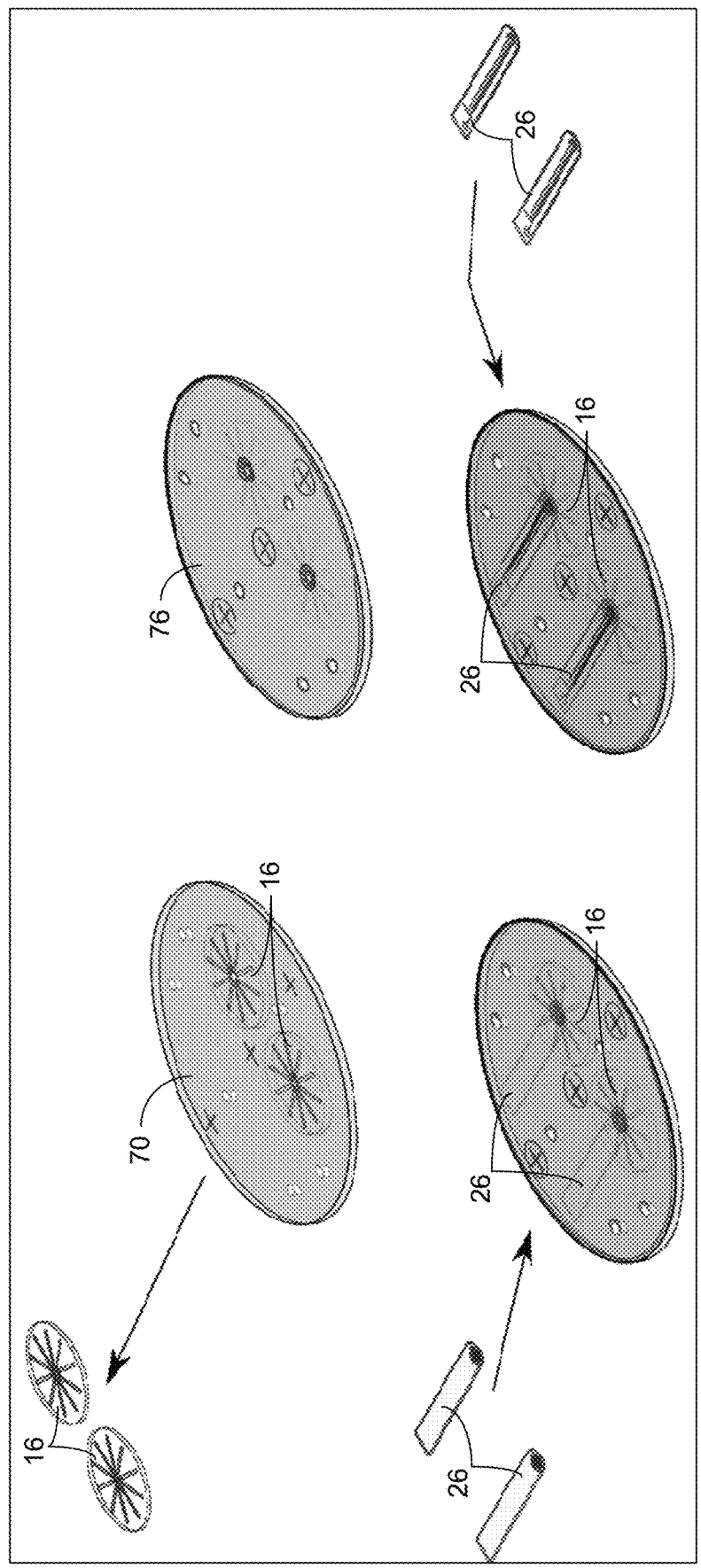
Figure 37:
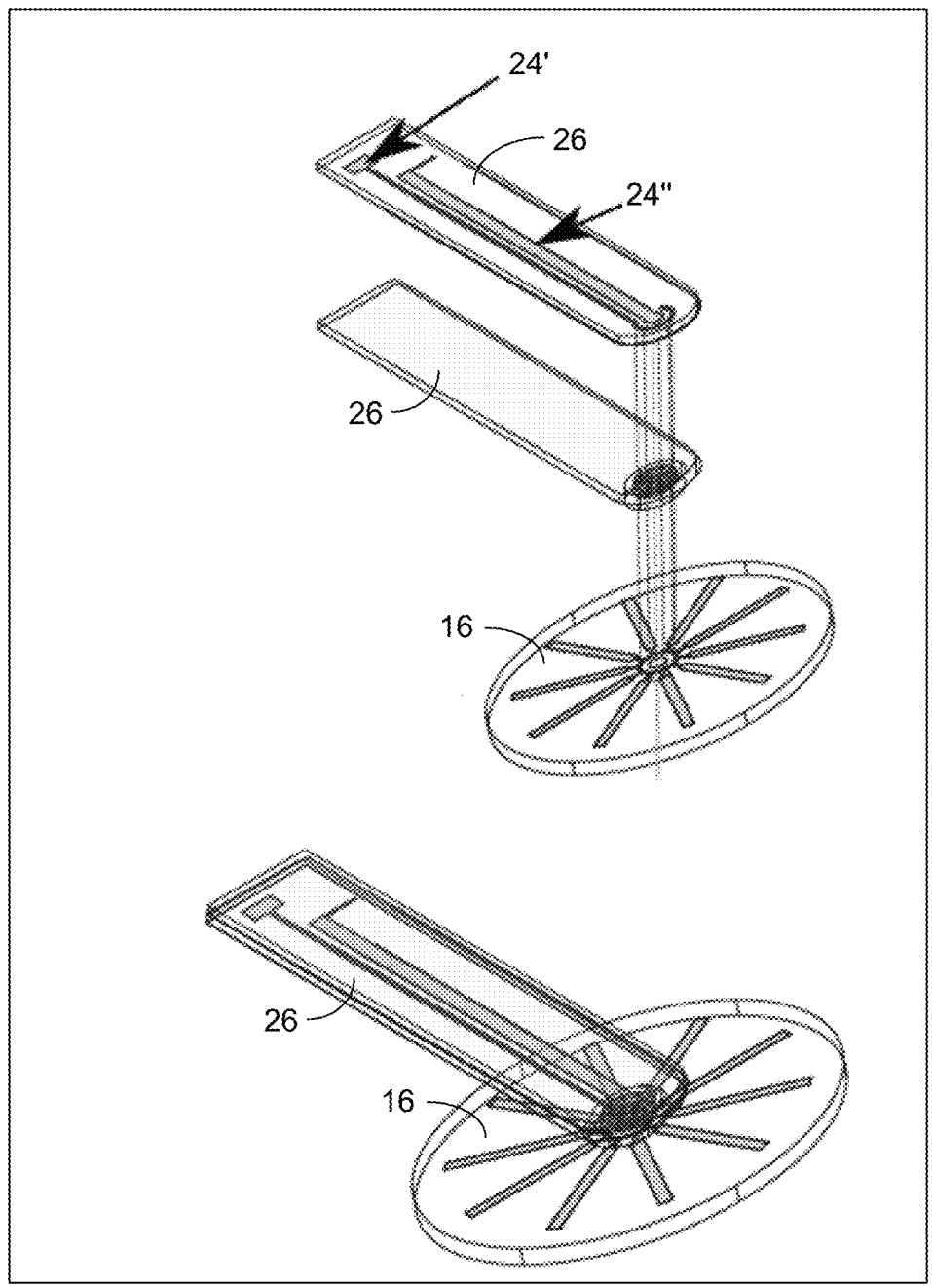

FIGS. 35-37 illustrate the layers and steps in a fabrication process for producing a laminate soft gripper device.

Figure 38:
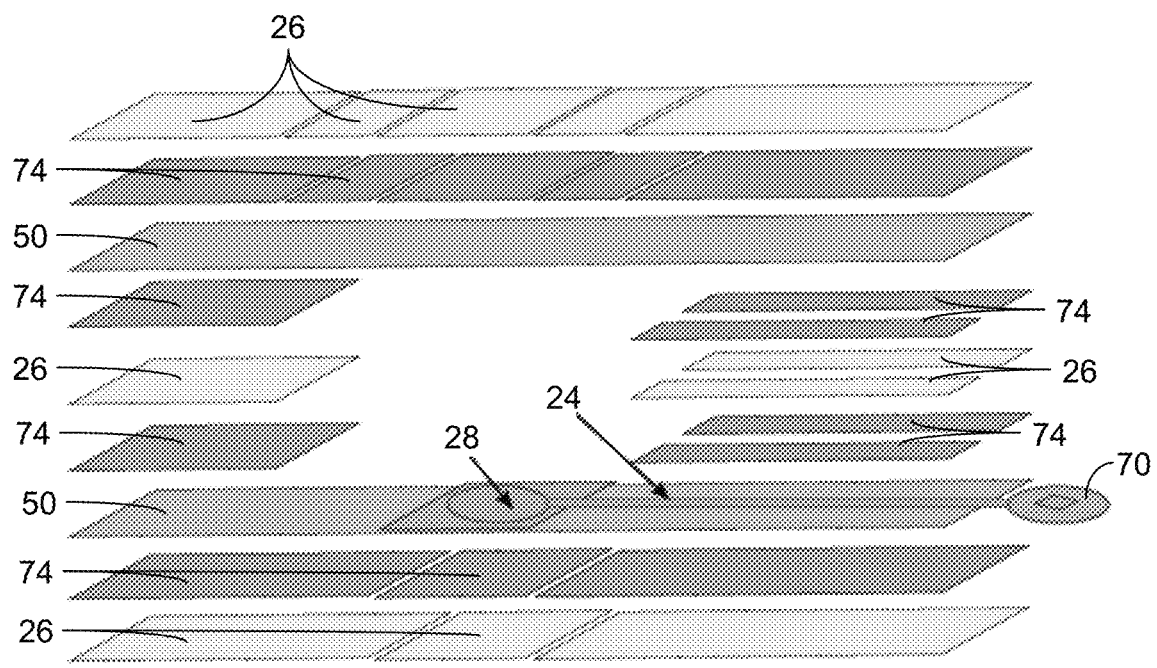

FIG. 38 is an exploded view of a laminate structure for an internal micro-balloon joint (IMJ).

Figure 39:
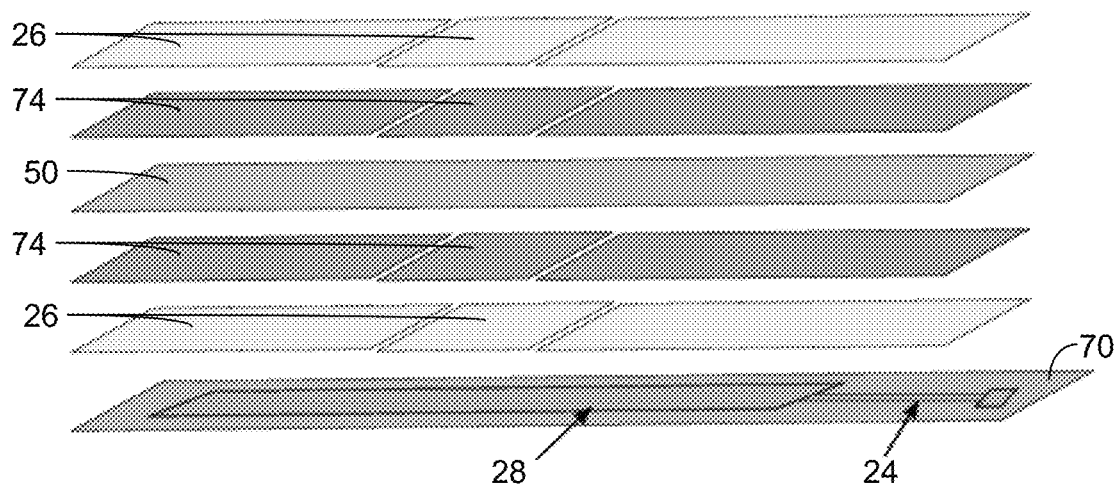

FIG. 39 is an exploded view of a laminate structure for an external micro-balloon joint (EMJ).

In the accompanying drawings, like reference characters refer to the same or similar parts throughout the different views; and apostrophes are used to differentiate multiple instances of the same or similar items sharing the same reference numeral. The drawings are not necessarily to scale; instead, an emphasis is placed upon illustrating particular principles in the exemplifications discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially (though not perfectly) pure, as practical and imperfect realities may apply; e.g., the potential presence of at least trace impurities (e.g., at less than 1 or 2%) can be understood as being within the scope of the description. Likewise, if a particular shape is referenced, the shape is intended to include imperfect variations from ideal shapes, e.g., due to manufacturing tolerances. Percentages or concentrations expressed herein can be in terms of weight or volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

Herein, soft elastomeric materials are integrated in a pop-up MEMS fabrication process, wherein the teachings of, e.g., U.S. Pat. No. 8,834,666 B2 and WO 2015/020952

Figure 1:
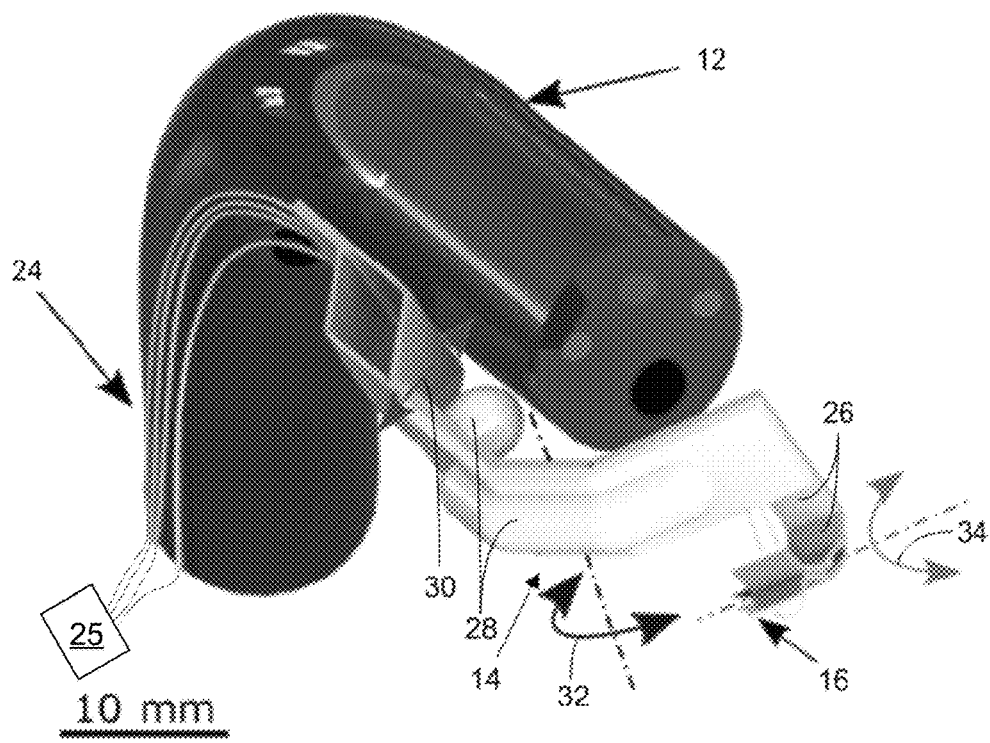
FIGS. 1 and 2 are illustrations, from two perspectives of a combination of soft pop-up mechanisms that form an articulated mechanism at the tip of an endoscope to provide additional dexterity and manipulation capabilities during endoscopic procedures.
Figure 2:
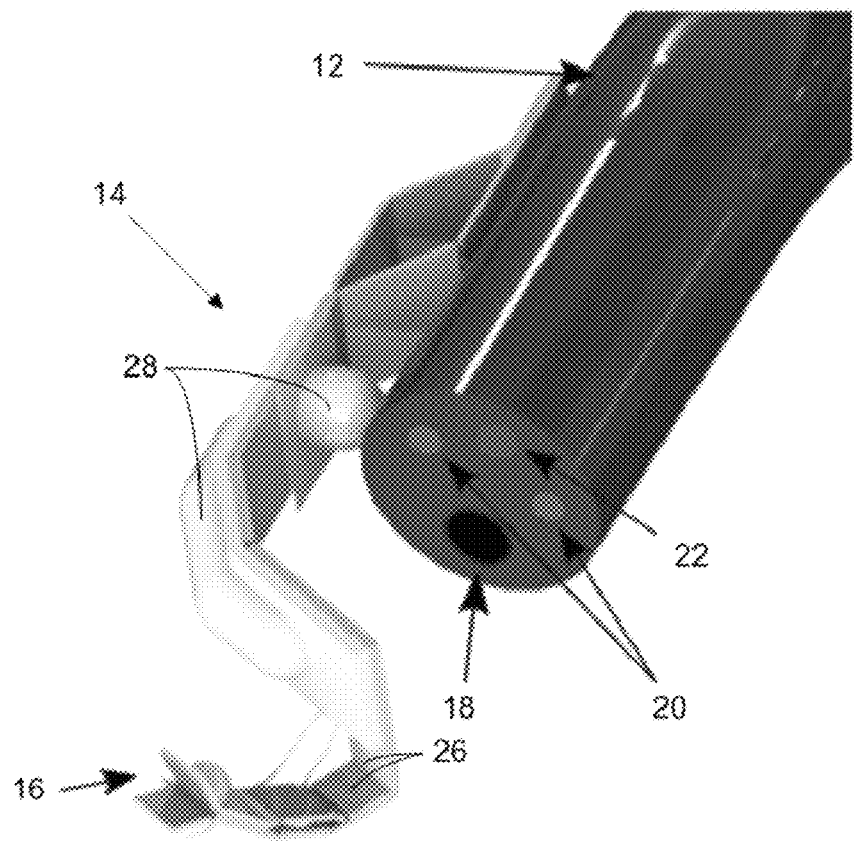

A1 can also be utilized, to create multilayer rigid-flex laminates and soft fluidic micro-actuators to demonstrate the possibility of developing simple sensors and actuators at millimeter scales. Additionally, the use of balloon actuators with multilayer rigid-flex laminates is described in U.S. Patent Application No. 62,212,757. Finally, based on the results obtained from the characterization of the micro-actuators developed, multiple actuators are assembled into a multi-articulated robotic arm (FIGS. 1 and 2). In an exemplification such as that illustrated in FIGS. 1 and 2, such an arm can provide additional dexterity and manipulation capabilities during endoscopic procedures when integrated on the tip of the endoscope.

As seen in FIGS. 1 and 2, the endoscope 12 includes an elongated deformable body formed, e.g., of a soft polymer. This body defines a working channel 18 and channels for light emitting diodes (LEDs) 20 and a vision system 22. Fluid lines 24 coupled with a fluid source 25 provide fluid (e.g., gas or liquid) activation of the balloons 28, which displace the laminate linkage 14 via an extension (expansion) 30 of the linkage 14 or via a change of yaw 32 or pitch 34. An end effector 16 (here in the form of a gripper) can be provided at the end of the laminate linkage 14 to grip or manipulate objects.

Design and Fabrication

In the following section, the integration of soft materials and soft fluidic micro-actuators into the pop-up MEMS fabrication process is discussed. Benefits of this approach include providing a soft interface between the mechanisms and the tissue, smoothing of sharp edges resulting from the lamination process, and exploiting soft fluidic actuation in order to build instruments that can safely interact with soft tissue. Furthermore, integrating soft actuators inside a kinematically constrained structure can potentially improve actuation reliability and predictability (relative to fully soft mechanisms). Three example mechanisms are proposed: two bending actuators and one linear actuator with proprioceptive capacitive sensing. To pursue this approach, the following two technical challenges are solved: realizing soft fluidic micro-actuators that can withstand high deformations and bonding the soft material to the rigid laminates.

A. Fabrication of Soft Fluidic Micro-Actuators

The soft fluidic micro-actuators can be fabricated using soft lithography. This technique typically utilizes polydimethylsiloxane (PDMS) that is spun onto silicon molds and thermally cross-linked, thus resulting in layers that can be adhered and sealed irreversibly via oxygen plasma treatment [see D. Qin, et al., "Soft lithography for micro- and nanoscale patterning," 5 Nature protocols 491-502 (2010)]. In order to increase the resistance of PDMS to deformation under the pressure that is necessary to actuate pop-up based mechanisms, PDMS (e.g., SYLGARD 184 silicone elastomer from Dow Corning Corp., Auburn, Michigan, USA) is mixed with, e.g., DRAGON SKIN 0020 silicone rubber (from Smooth-On, Inc., Macungie, Pennsylvania, USA), providing a mixture of silicone elastomers across a range of hardnesses or elastic moduli. Via this mixture, a material is obtained that still allows fabrication of micrometer-scale feature sizes and, at the same time, withstands large deformations. Layers of different mass ratios of PDMS and silicone rubber can then be bonded together via oxygen plasma treatment to build balloon actuators capable of directional deformation.

Figure 3:
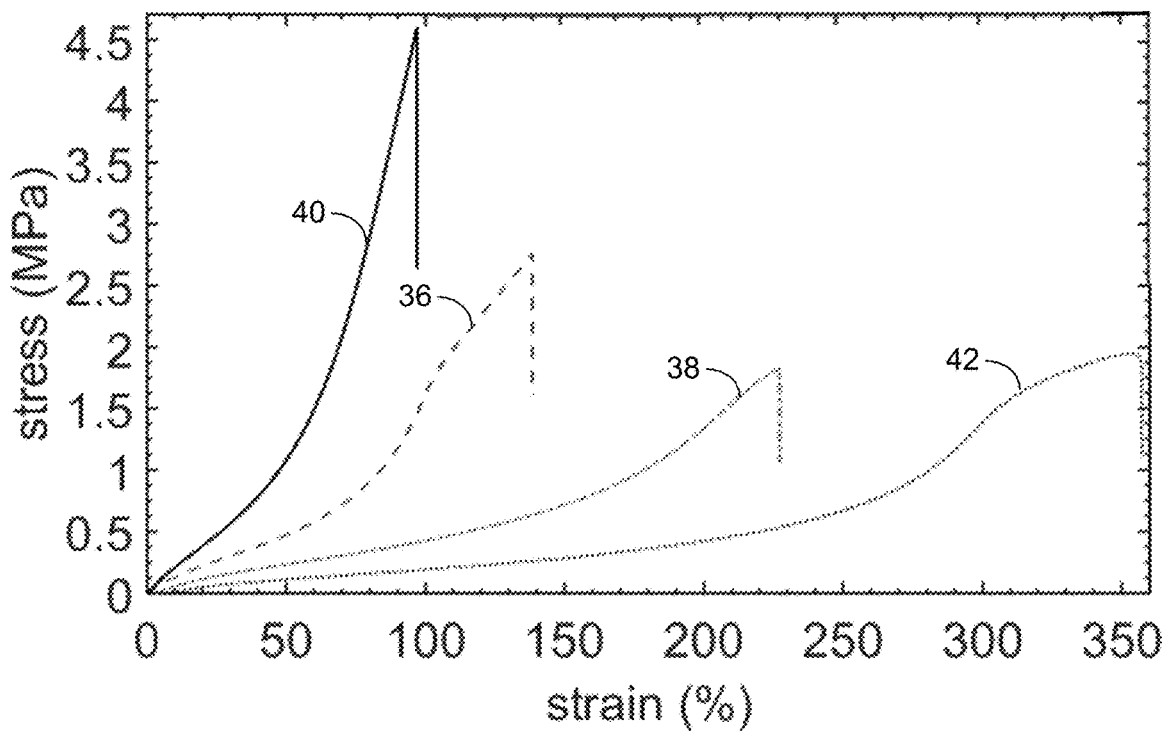
FIG. 3 is a plot of results from stress-strain tests of PDMS, silicone rubber, a mixture of PDMS and silicone rubber at a 1:1.5 ratio, and a mixture of PDMS and silicone rubber at a 1:3 ratio.

In particular embodiments, stiffer layers were fabricated using a 1:1.5 mass ratio (PDMS:DRAGON SKIN 0020 silicone rubber) 36 in combination with softer layers using a 1:3 mass ratio (PDMS:DRAGON SKIN 0020 silicone rubber) 38. Stress-strain tests of these soft composites 36 and 38, performed according to ISO 37:2005(E), are reported in FIG. 3 along with stress-strain tests of PDMS 40 and DRAGON SKIN 0020 silicone rubber 42, alone. The mass ratio of 1:3 is the maximum amount of DRAGON SKIN 0020 silicone rubber that can be added to the polymeric mixture while preserving the capability of sealing layers via oxygen plasma. The effect of adding the silicone rubber to the mixture is to increase the strength to failure and decrease the stiffness, as is evident from FIG. 3.

DRAGON SKIN 0020 silicone rubber, however, may not be entirely advantageous for use in medical/surgical applications due to biocompatibility issues. Consequently, a medical-grade silicone elastomer [e.g., MED4-4220 (17 A durometer), MED-4011 (27 A durometer), MED-4044 (40 A durometer), and MED-6033 (50 A durometer) silicone elastomers available from NuSil Technology of Carpinteria, California, US] can be used as an alternative. These silicone elastomers are more stretchable and have a higher tear strength than SYLGARD 184 silicone elastomer. Where biocompatibility (e.g., reducing the risk of cytotoxicity) is particularly targeted, any of the above-referenced medical-grade silicone elastomers can be used in combination with 9877 medical adhesive from 3M Corp. and 0.254-mm-thick and 0.025-mm-thick optically clear polyester sheets for the rigid plates 26 and flexure layers 50, respectively, which are also biocompatible.

Figure 4:
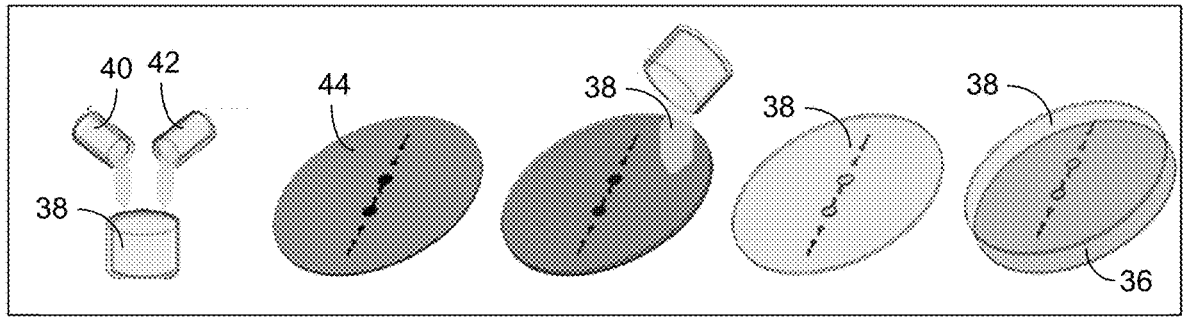
FIGS. 4-7 provide schematic illustrations of a fabrication and integration process for soft fluidic micro-actuators.
Figure 5:
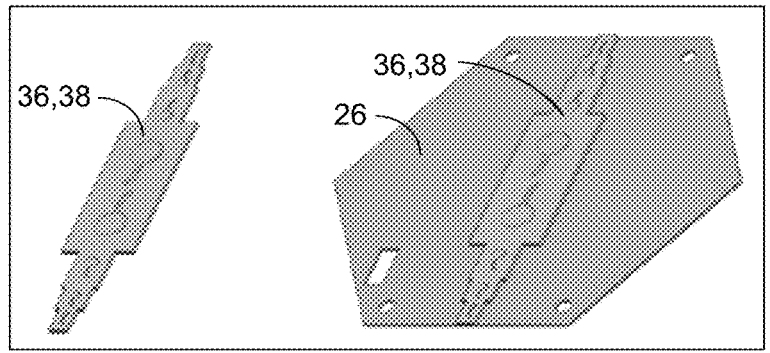

A fabrication process for forming the soft fluidic micro-actuators is illustrated in FIGS. 4-7. PDMS 40 and silicone rubber 42 are mixed, as shown in FIG. 4, using a 1:3 ratio, and the mixture 38 is spun coat onto a silicon wafer 44 patterned (where the height of features is approximately 80 μm) with SU-8 photoresist (from MicroChem Corp., Westborough, MA, USA) at 270 revolutions per minute (rpm) for 60 seconds (resulting in a 0.25 mm thick membrane). The patterned layer 38 of PDMS and silicone rubber is thermally cross-linked for 30 minutes, peeled from the wafer 44 and bonded via oxygen plasma treatment on an unpatterned layer made using a 1:1.5 ratio of PDMS and silicone rubber 36, which is spun at 150 rpm for 60 seconds (for a 0.6-mm thickness).

Figure 6:
Figure 7:
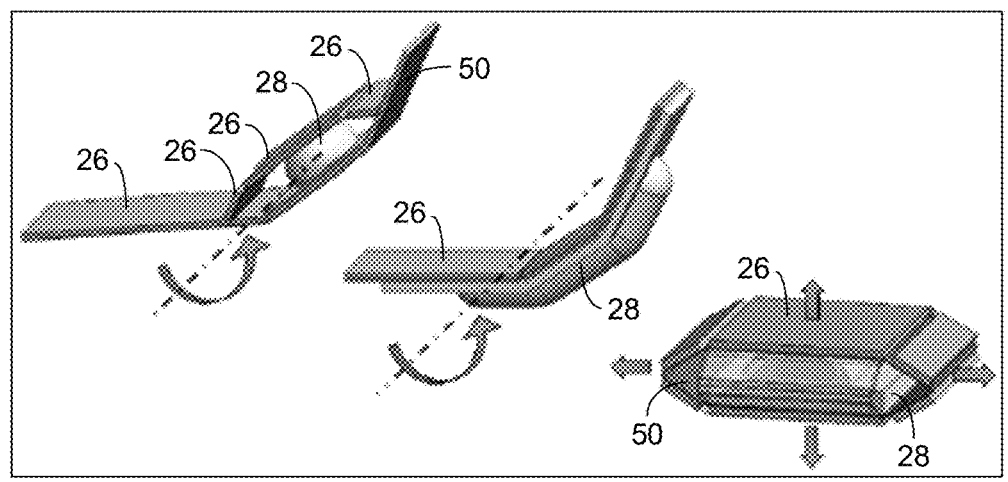

The micro-structures 36, 38 are then cut and bonded irreversibly via oxygen plasma treatment to a hard (rigid) material 26 (e.g., laser-machined metal and/or plastic) having a surface that was previously functionalized—i.e., activated by oxygen plasma followed by (3-Aminopropyl)triethoxysilane (APTES coupling agent, Sigma-Aldrich Corp., St. Louis, Missouri, USA) modification (see FIG. 5), as described in V. Sunkara, et al., "Versatile method for bonding hard and soft materials," 2 Rsc Advances 9066-9070 (2012). Through this approach, an irreversible bond is obtained at the interface between the soft 36, 38 and hard 26 material without the need for using additional adhesives. The resulting composite material can easily be integrated in the pop-up MEMS fabrication process, realigned with the other laser-machined rigid-flex laminates to be bonded in a heated press with DuPont FRO100 sheet adhesive (spacer materials, in the form of additional rigid plates 26, can be inserted to match the height of the soft layers 36, 38 and to help better distribute the pressure on the adhesive during curing), as shown in FIG. 6. As shown in FIG. 6, at least one flexure layer 50 (formed, e.g., of polyimide film or other material that is substantially more flexible than the rigid plates 25) is included in the laminate to provide for flexure at gaps between rigid plates 26. The resulting laminate is laser machined to release the final mechanisms; tubes 24 (shown in FIGS. 1 and 2) with inner diameter of 254 mm (e.g., Micro-Renathane Catheter Tubing from Braintree Scientific, Inc., Braintree, Massachusetts, USA) are inserted and sealed (LOCTITE PDXY PAK epoxy from Henkel AG & Co., Dusseldorf, Germany); and the soft fluidic micro-actuator balloons (formed from the PDMS/silicone rubber layers 36 and 38) are pressurized to pop-up and expand the folded mechanisms (formed of rigid plates 26 joined by the flexure layer 50) and thereby provide actuation (see FIG. 7).

B. Design of Soft Pop-Up Micro-Mechanisms

Figure 8:
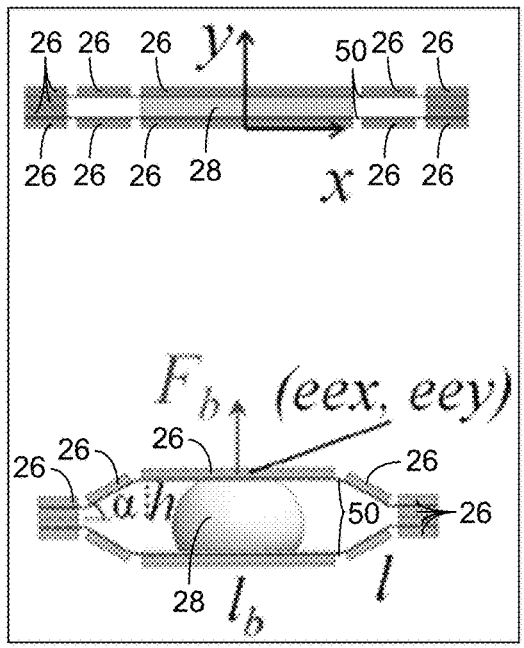
FIGS. 8-12 illustrate three proposed soft pop-up mechanisms.
Figure 9:
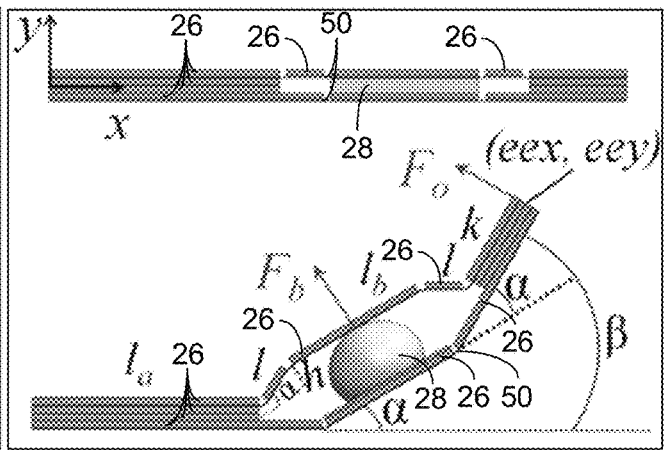
Figure 10:
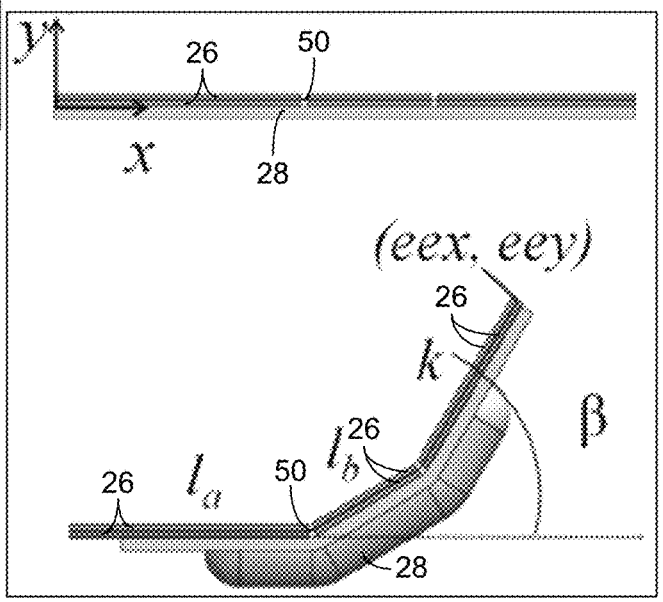

A linear actuator that can be used for expansion/stabilization mechanisms and injection tasks as well as bending actuators that can be exploited for surgical tasks, such as tissue retraction and cutting or steering an endoscopic instrument, are presented in the following section. The linear actuator of FIG. 8 is based on a Sarrus linkage mechanism with an embedded soft micro-actuator balloon 28. The bending actuator of FIG. 9 is based on the same Sarrus linkage mechanism; but, in this case, the two bottom side plates 26 are fixed to convert axial deformation of the inner actuator into bending motion, thus we refer to this mechanism as an internal micro-balloon joint (IMJ). A second bending actuator (see FIG. 10) includes a series of linkages actuated by an external soft balloon 28, thus we refer to it as an external micro-balloon joint (EMJ). These actuators may have a length of, e.g., less than 4 cm, less than 2 cm in length, or, in particular embodiments, a length of ~1 cm or less.

Exploded views of the layers that form IMJ and EMJ laminate linkages 14 when pressed together are provided, respectively in FIGS. 38 and 39. The laminates include the following layers: silicone elastomer 70, in which one or more fluidic lines 24 and balloons 28 are defined; adhesive film 74; rigid plates 26; and flexure layers 60.

In one embodiment, the mechanisms are made of the following laminated components: 254-μm-thick fiberglass-reinforced epoxy laminate sheets (e.g., GAROLITE laminate) as structural material for the rigid plates 26, which are substantially inflexible at the actuation forces provided by the balloons 28; 25-μm-thick DuPont FR0100 sheet as adhesive (in alternative embodiments, 9877 pressure-sensitive transparent polyester double-sided medical tape from 3M Corp. of St. Paul, Minnesota, USA, can be used as the adhesive); and 25-μm-thick polyimide film as flexure layers 50 that flex between rigid plates 26 to perform essentially as "joints," though not as perfect joints that pivot entirely about a single axis. For the linear actuator, DuPont PYRALUX copper/polyimide (18-μm-thick copper and 25-μm-thick polyimide) is patterned to have conductive inner electrodes on the top and bottom, thus forming a capacitive sensor for detecting forces or for determining position. The kinematics of the linear actuator can be described by the following geometric model:

$$\begin{bmatrix} eex \\ eey \end{bmatrix} = \begin{bmatrix} 0 \\ 2l\sin\alpha \end{bmatrix},$$

where eex and eey represent the coordinates of the end effector in FIG. 8. To equate the input pressure to deformation of the actuators, Laplace's law is used for a thin-walled sphere (see FIG. 11) to obtain:

$$F_b = P2\pi R^2 - 2\pi r t E \left( \frac{\Delta R}{R_0} \right),$$

where P is the pressure inside the balloon 28; E is the elastic modulus of the material (experimentally derived by material characterization, see FIG. 3), r is the balloon diameter when not inflated, t is the thickness of the balloon membrane, and R is the total deformation of the balloon 28 in the axial direction (that equals 2 h in FIG. 8). In addition, σ is substituted (see FIG. 11) as follows:

$$\sigma = E \frac{\Delta R}{R_0}.$$

The actuation force is, therefore, directly related to pressure and balloon expansion. The balloon expansion can then be related to the pressure by applying membrane theory for a circular plate as follows:

$$h = \left( \frac{Pr^4}{128 \left( \frac{Et^3}{12(1-v)} \right)} \right),$$

where v is the Poisson's ratio of the polymeric material.

Dimensions of the fabricated prototype are as follows: $l_b$=3 mm; total thickness=1.157 mm (including a 0.85 mm thick soft actuator composed of 0.25 mm for the layer of 1:3 PDMS:DRAGON SKIN 0020 silicone rubber ratio and 0.6 mm for the layer of 1:1.5 ratio of these some components); and the soft actuator diameter, when not inflated, is 2.5 mm.

For the IMJ, the total bending range, β, is calculated as follows:

$$\beta = 2 \sin^{-1}(h/l),$$

where h is half of the micro-balloon expansion, and l is the length of the lateral plate of the Sarrus linkage. For this actuator, four prototypes are fabricated at different dimensions (reported in Table I, below) to evaluate scaling effects: $l_b$ (central plate) and l (lateral plate) are shown in FIG. 9, and f is the diameter of the non-inflated balloon. For each of the prototypes, the total thickness of the laminate is 1.167 mm; the height of the soft actuator, when not inflated, is 0.8 mm (0.25 mm for the layer of 1:3 PDMS:DRAGON SKIN 0020 silicone rubber ratio and 0.55 mm for the layer of 1:1.5 ratio of these same components). For this mechanism, the force, $F_b$, exerted by the micro-balloon on the central plate can be geometrically related to the output force, $F_0$, generated at the tip of the system as follows:

$$F_0 = F_b \left( \frac{1}{1+k} \right) \cos\alpha,$$

where a and k are shown in FIG. 9, and where $F_b$ is the same as for the linear actuator. The equation describing the trajectory of the end effector (eex, eey) is reported for the structure in FIG. 9 as a function of design parameters as follows:

$$\begin{bmatrix} eex \\ eey \end{bmatrix} = \begin{bmatrix} 1_a + 1 + \cos\alpha(1_b + \sin\alpha(1 + k)) \\ \sin\alpha(1_b + \cos\alpha(1 + k)) \end{bmatrix}.$$

TABLE I

Dimensions of the Fabricated IMJ and EMJ Prototypes

| IMJ | $l_b$(mm) | l(mm) | φ(mm) |
|---|---|---|---|
| | 5 | 1.34 | 3 |
| | 2.5 | 0.55 | 1.3 |
| | 1.75 | 0.5 | 0.85 |
| | 1 | 0.324 | 0.53 |
| EMJ | $l_b$(mm) | balloon length (mm) | balloon width (mm) |
| | 5 | 19 | 3 |
| | 2.5 | 10.45 | 1 |
| | 1.75 | 7 | 0.9 |
| | 1 | 6 | 0.8 |

Figure 11:
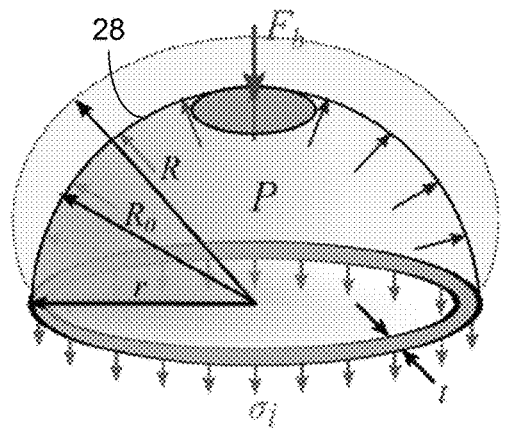
Figure 12:
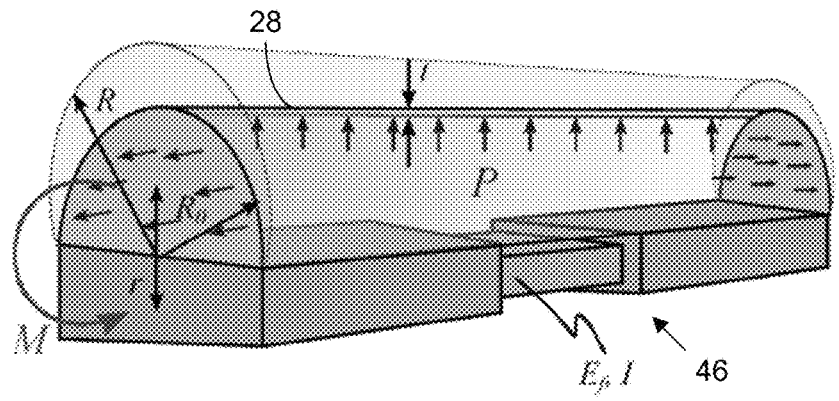

The actuator of FIG. 11 is axial fully soft actuator with a circular cross-section chamber that expands into a hemispherical balloon upon pressurization with fluid (e.g., water), while the actuator of FIG. 12 is a bending fully soft actuator with a rectangular chamber that allows bending based on layer and material asymmetry. Biocompatible silicone elastomers can be used to form the layers that form the actuators.

Four prototypes are fabricated at different dimensions for the EMJ, as well. Dimensions are reported in Table I, above, for $l_b$ (central plate length) and for the length and width of the non inflated balloon. For each of the prototypes, the total thickness of the rigid laminate (plate) is 0.575 mm, the thickness of the soft actuator is 1.15 mm (0.45 mm for the layer of 1:3 PDMS:DRAGON SKIN 0020 silicone rubber ratio and 0.7 mm for the layer of 1:1.5 ratio of these same components). The total bending, β, of this mechanism can be related to the torque generated, M, to the input pressure by using the Law of Laplace and modeling the polyimide flexure as a beam 46 (see FIG. 12):

$$P = \frac{Et}{2R}\left(\frac{\Delta R}{R_0}\right),$$
$$M = 2\pi R^2 Pr, \text{ and}$$
$$\beta = -\left(\frac{M}{E_f I}\right),$$

where $E_f$ is the elastic modulus of polyimide.

C. Design of a Soft Pop-Up Multi-Articulated Robotic Arm

Based on the design of the soft pop-up mechanisms presented in FIGS. 8-12, a simple system integrating multiple degrees of freedom (DOFs) is designed. The structure 14, integrated at the tip of an endoscope 12 (see FIGS. 1 and 2), is composed of a four-bar linkage mechanism for expansion, thus allowing surgical triangulation, a yaw 32 degree of freedom (DOF) (based on the design of FIG. 10), and a pitch 34 DOF (based on the mechanism of FIG. 9) to steer the end effector 16 and perform tissue manipulation. The first two mechanisms are 5-mm wide, while the third is 2.5-mm wide. The total length is 35 mm, coming out of the tip of the endoscope by 12 mm. The thickness of the structure 14 is equal to one of the single mechanisms. Such a structure is presented as a demonstration of how to integrate the multiple elements described in this paper and as a proof of concept that articulated medical instruments can be designed exploiting the proposed soft pop-up technology.

Experiments

The linear actuator is characterized in terms of capacitance variation as a function of the distance between the plates. The two bending actuators are experimentally characterized to determine the maximum torque generated in isostatic conditions and the maximum free bending angle. An evaluation platform with a linear stage actuating a syringe 1 mm/s corresponding to a water flow of 0.01 ml/s is designed and fabricated in order to test the mechanisms. Pressure, force, and capacitance data are acquired using a NI USB-6002 board; and data collection is performed in LabVIEW software (National Instruments, Austin, TX, USA).

Capacitance Variation Characterization

Capacitance variation versus increasing distance between the conductive plates is measured by applying increasing pressures through the same setup and measuring the capacitance through an AD7746 evaluation board (Analog Devices, Norwood, MA, USA) with the following specifications: resolution=4 aF, accuracy=4 fF, and update rate=50 Hz.

Torque Characterization

Torque characterization is performed by placing the joints in a straight configuration (0° bending), constraining one side, and placing the other in contact with a force/torque (F/T) sensor (a NANO17 F/T sensor from ATI Industrial Automation, Apex, North Carolina, USA). Torque is computed by multiplying the measured force by the moment arm (i.e., the distance between the center of the central plate and the point of contact with the F/T sensor). Tests are repeated three times for each joint, and two joints of each size are tested. The IMJ is tested for pressures up to 500 kPa, while the EMJ is tested up to 200 kPa. The pressure limits are chosen to minimize the risk of failure, as pressures in the same range have already been safely tested in devices for minimally invasive surgery (MIS). Pressure is recorded using a pressure sensor (a BSP B010-EV002-A00A0B-54 pressure sensor from Balluff Inc, Florence, Kentucky, USA).

Bending Characterization

The bending characterization is performed by applying increasing pressure in the joints and resolving the correspondent bending angle visually. Images are taken by placing a camera on a tripod parallel to the joint and analyzed with MATLAB software (Mathworks, Inc., Natick, Massachusetts, USA). The IMJ is tested for pressures up to 350 kPa, while the EMJ is tested up to 200 kPa. Also in this case pressures are chosen in order to safely and repeatedly test the samples with low risk of failure or leakages.

Multi-Articulated Robotic Arm Demonstration

The multi-articulated robotic arm is mounted on top of an endoscope model (with a 10-mm outer-diameter diameter tube) to demonstrate the capability of performing the following simple potential surgical tasks: expanding the mechanism to perform triangulation, actuating the yaw DOF to steer the end effector, and actuating the pitch DOF to approach tissue.

Results and Discussion

Figure 13:
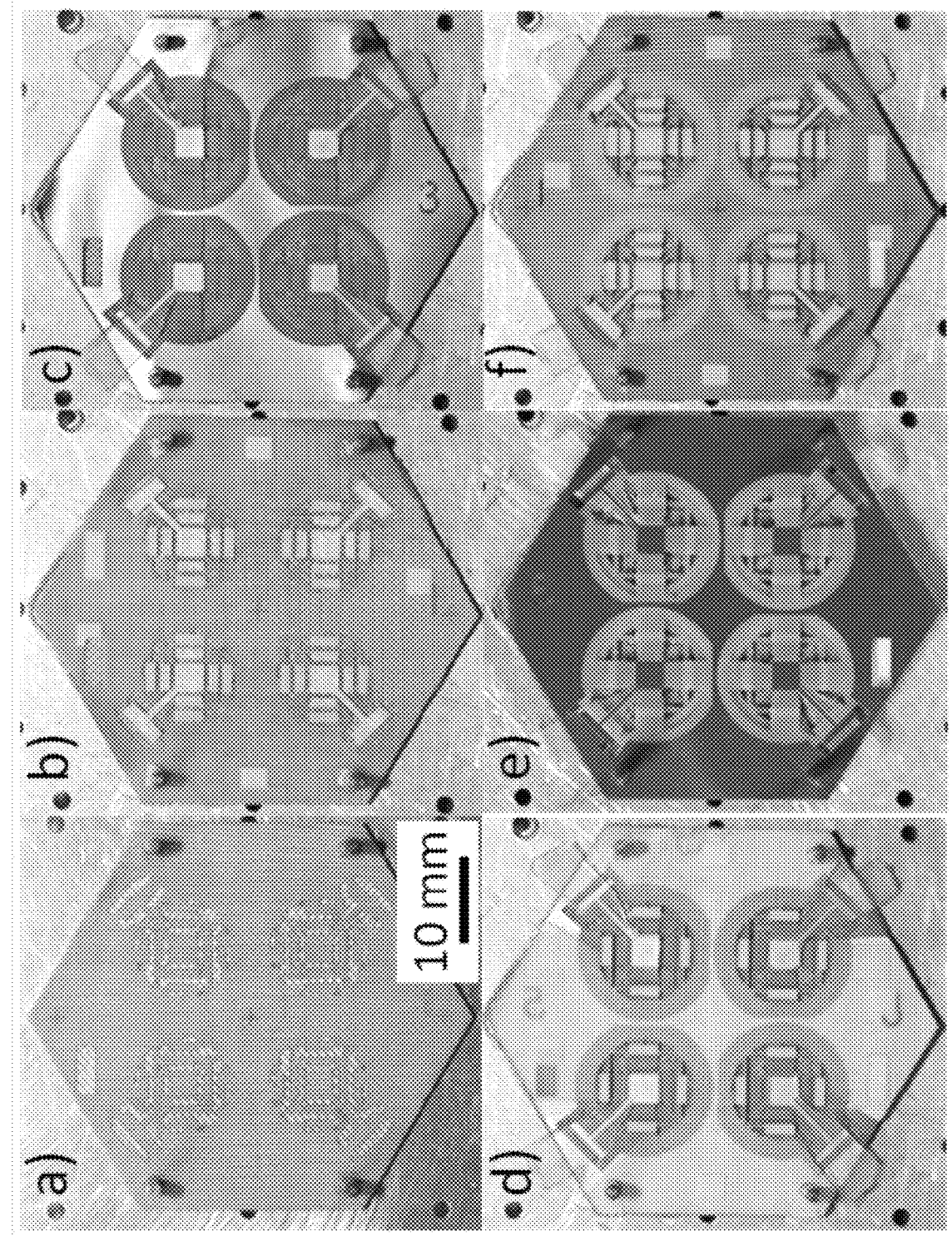
FIG. 13, which includes photographic images a-f, shows a fabrication process of a soft pop-up linear actuator with proprioceptive sensing. In image a, rigid laminates are aligned using precision dowel pins. In image b, a 25-m DuPont FRO100 sheet adhesive is applied to a laminate. The composite layer of soft and rigid material is then integrated in image c. In image d, spacers are then inserted through the composite laminate; and, in images e and f, the lamination continues until the all of the necessary layers are inserted.

Fully functional prototypes have been fabricated and tested. Since each of the mechanisms follow the same fabrication process (as shown in FIGS. 4-7), only the fabrication steps for the linear actuator are presented in FIG. 13.

Capacitance Variation Characterization

Figure 14:
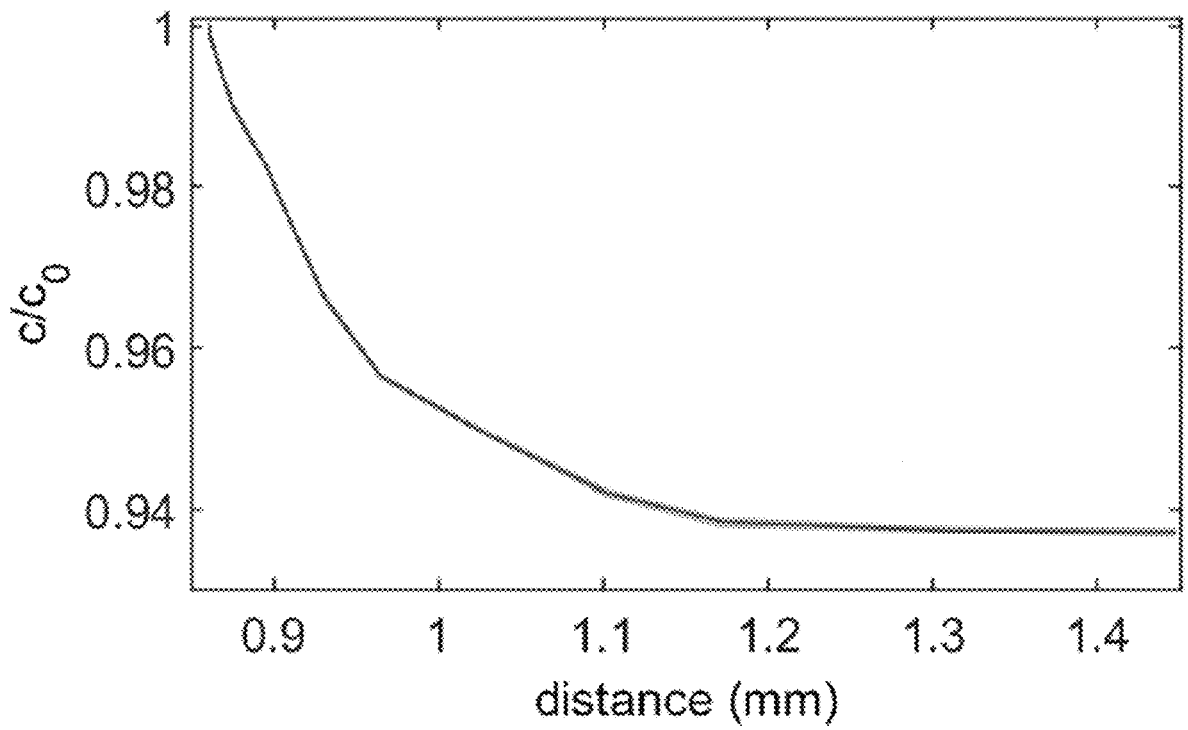
FIG. 14 plots the results of the capacitance characterization during actuation of a linear actuator with insets respectively showing the linear actuator prototype unactuated and actuated states.

The capacitance measured during actuation of the linear actuator is reported in FIG. 14, which plots the mean value of the capacitance during actuation of the linear actuator. The capacitance is normalized in order to more easily compare different prototypes. A maximum capacitance variation of 0.21 pF is observed with a linear actuation of up to 1.45 mm.

Torque Characterization

Figure 15:
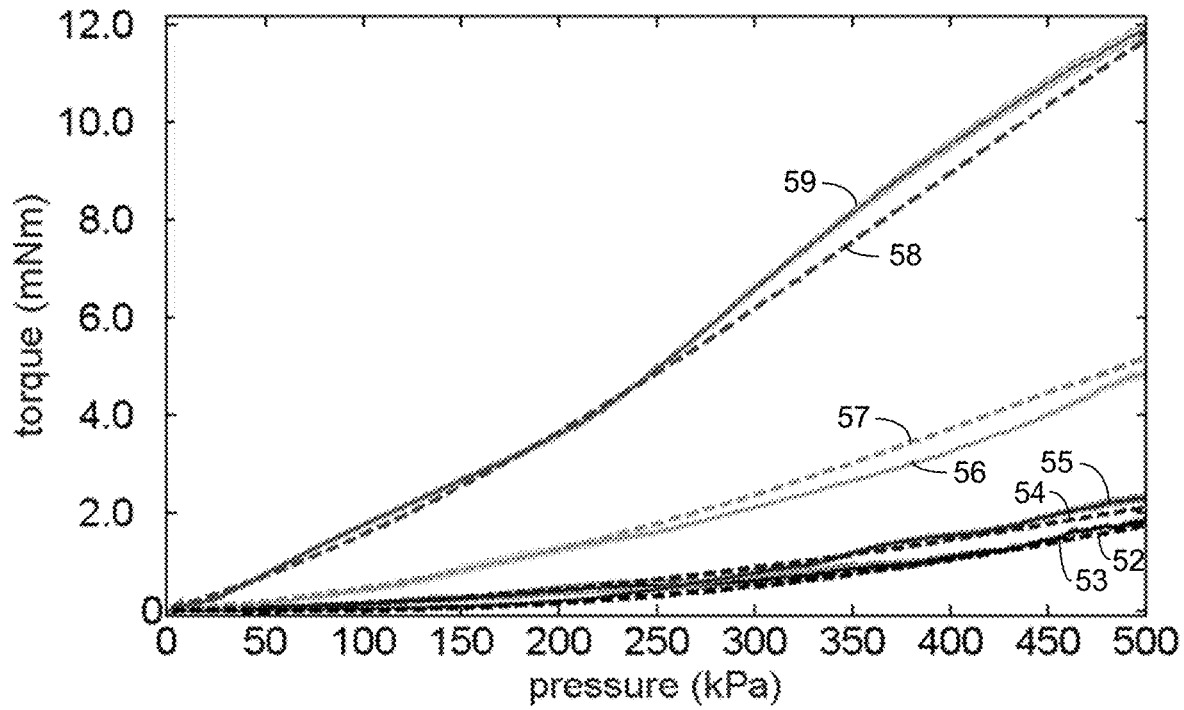
FIG. 15 plots the results of a torque characterization test for internal micro-balloon joint (IMJ) prototypes fabricated at different scales with different central-plate lengths ($l_b$). The dashed lines represent the output from the model, while the solid lines represent the mean values; and the shaded area represents one standard deviation computed on two prototypes for each size, tested three times each.
Figure 16:
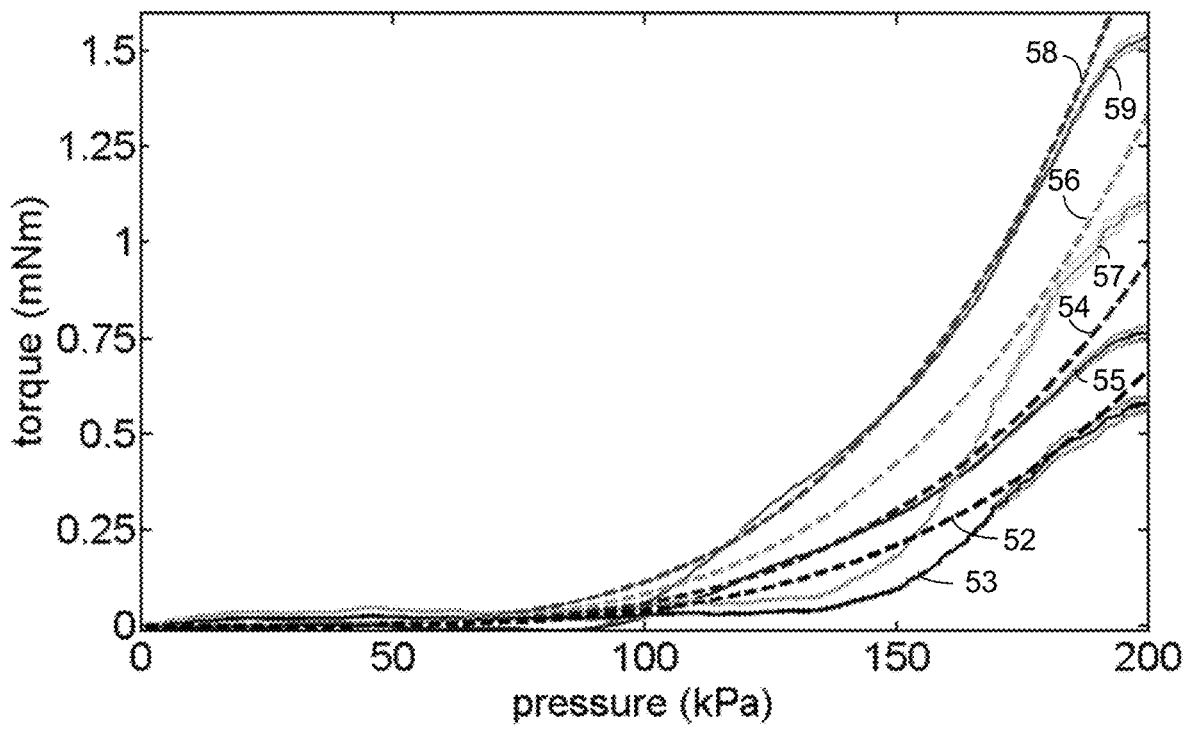
FIG. 16 plots the results of a torque characterization test for external micro-balloon joint (EMJ) prototypes fabricated at different scales ($l_b$). The dashed lines represent the output from the model, while the solid lines represent the mean values; and the shaded area represents one standard deviation computed on two prototypes for each size, tested three times each.

Torque characterization results are reported in FIG. 15 and in FIG. 16, respectively, for the IMJ and EMJ prototypes fabricated at different scales ($l_b$). On the same plots, the results are from the analytical model described in the "Design of soft pop-up micro-mechanisms" section, above. In each of FIGS. 15 and 16, lines 52 (for $l_b$=1 mm), 54 (for $l_b$=1.75 mm), 56 (for $l_b$=2.5 mm) and 58 (for $l_b$=5 mm) represent the output from the model; and lines 53 (for $l_b$=1 mm), 55 (for $l_b$=1.75 mm), 57 (for $l_b$=2.5 mm), and 59 (for $l_b$=5 mm) represent the mean values, while the shaded area represents one standard deviation computed on two prototypes for each size, which are tested three times each. The picture in the inset shows the actuator during the test.

The model is able to predict the experimental data quite accurately both for the IMJ and for the EMJ. In the case of the EMJ, the model tends to overestimate at higher pressures most likely because, in that case, the balloon tends to expand more radially than axially, thus contributing less to the torque. The numerical values from the experiments are reported in Table II, below.

TABLE II

Torque and Bending Characterization Results. Forces are computed considering the arm as half of the central plate ($l_b$) plus 2.5 mm (k in FIGS. 9 and 10)

| | $l_b$ (min) | Max torque (mNm) | Force (N) @k = 2.5 mm | Max bending angle (°) |
|---|---|---|---|---|
| IMJ | | | | |
| | 5 | 11.9 ± 0.1 | 2.4 | 66.3 ± 1.4 |
| | 2.5 | 4.9 ± 0.1 | 1.3 | 73.8 ± 1.6 |
| | 1.75 | 2.3 ± 0.1 | 0.68 | 42.6 ± 1.6 |
| | 1 | 1.8 ± 0.1 | 0.5 | 21.1 ± 1.2 |
| EMJ | | | | |
| | 5 | 1.53 ± 0.02 | 0.3 | 89.4 ± 2.1 |
| | 2.5 | 1.11 ± 0.03 | 0.2 | 77.8 ± 0.9 |
| | 1.75 | 0.77 ± 0.03 | 0.4 | 89.0 ± 2.4 |
| | 1 | 0.58 ± 0.02 | 0.2 | 55.7 ± 1.2 |

The IMJ is able to generate maximum torques ranging from 1.841±0.07 mNm to 11.87±0.12 mNm, depending on the size of the prototype. Depending on the arm length, relatively high forces can be obtained with the IMJ; for example, with the largest prototype, a force of 2.4 N can be generated with a 5-mm arm; and, with the smallest prototype, a force of 0.5N can be obtained with a 3.5-mm arm. In addition, it is worth noting that the IMJ can be tested up to 500 kPa, since the balloon is constrained not to expand by the surrounding pop-up structure; and, thus, the risk of failure due to large deformation of the soft actuator is reduced.

In the case of the EMJ, the balloon tends to expand in the direction of lower impedance (i.e., in an opposite direction from the load cell) and, thus, it is not able to safely reach the same pressure. The EMJ provides lower torques, between 1.5 and 0.6 mNm, resulting in forces on the order of hundreds of milliNewtons. In addition, the EMJ starts applying measurable forces on the F/T sensor after a pressure of 100 kPa is applied, since, before that pressure, the introduced fluid is mainly inflating the balloon in the lower-impedance direction (where it is not constrained by any surrounding pop-up mechanism).

Bending Characterization

Figure 17:
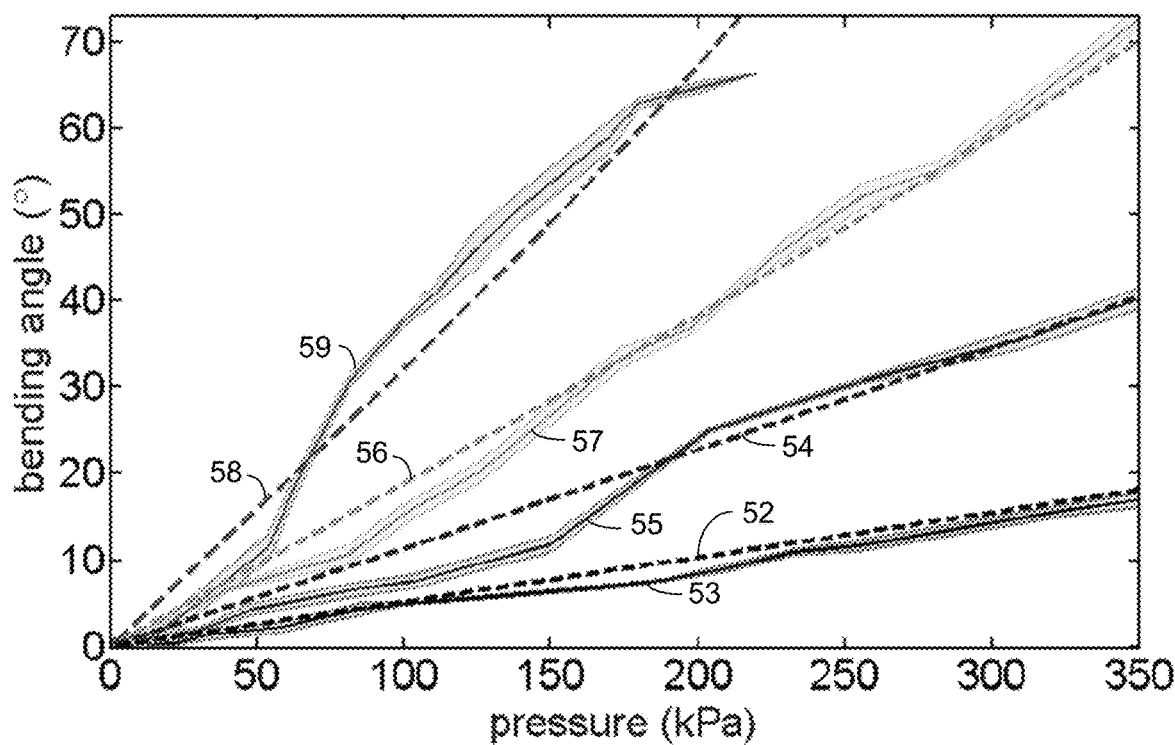
FIG. 17 plots the results of a bending angle characterization test for IMJ prototypes fabricated at different scales ($l_b$).

Bending angle characterization results are reported in FIGS. 17 and 18 for the IMJ and in FIGS. 19 and 20 for the EMJ. The model is able to follow the trend of the experimental data quite accurately, although it tends to overestimate the bending at lower pressures, likely due to the hyperelastic behavior of the elastomer, which is approximated as linear in the model. In the case of the larger joint, the model tends to overestimate the bending, probably because the balloon starts being more significantly bent; and, thus, the spherical approximation starts to fail. On the other hand, in the case of the EMJ, the model is not able to fully capture the trend of the experimental data. This failure is mainly due to lower accuracy in the integration of the actuator during fabrication (e.g., being not perfectly centered or aligned in some cases). In addition, the proposed model neglects the pressures acting in the radial direction (i.e., perpendicular to the plates of the EMJ). Despite this, the model can be exploited as a first order approximation of the system in the design process.

Numerical values of the maximum bending angles of the different actuators are summarized in Table II, above. In this case, the design of the EMJ provides higher bending capabilities, reaching almost 90°. The IMJ also provides large bending, around 60°. What seems to limit the bending capabilities of this design is that at higher pressure, the surrounding pop-up mechanism starts offering increasing resistance to the balloon expansion, which starts expanding laterally (pushing on the lateral plates) instead of axially. The current design controls bending by pressurizing the soft actuators with water and decreasing the bending angle by removing the water. The restoring motion relies mainly on the strain energy stored in the elastomer as well as on the incompressibility of water.

Multi-Articulated Robotic Arm Demonstration

FIGS. 21-24 show a multi-articulated robotic arm 14 based on soft fluidic micro-actuators and pop-up mechanisms. The proposed fabrication process enables integration of sensing capabilities; and a proof of concept of monitoring capacitance variation during actuation is successfully demonstrated along with the potential option of closed-loop control of the mechanisms using this embedded sensing. The presented mechanisms demonstrated forces and dexterity that render them suitable candidates for designing novel micro-surgical tools. Indeed, forces required in endoscopic procedures are typically below 1 N for endoluminal retraction tasks (i.e., tensioning the tissue for easing the cutting procedure). The potential of easily scaling down the mechanisms makes this technology promising for procedures that are currently difficult to perform in a minimally invasive way, such as interventional bronchoscopy.

The minimum tested operational frequency (to inflate the larger balloons) is 14 Hz with a flow rate of 0.01 ml/s in a 254-mm diameter pipe running along a 1-m long endoscope. A typical frequency range during microsurgical tasks is 0-1.7 Hz. Finally, the presented systems are integrated to fabricate a demonstration piece of a multi-articulated robotic arm that is mounted on top of an endoscope model to demonstrate simple tasks that can be useful in a surgical scenario, such as expansion of the mechanism to perform triangulation, yaw, and pitch so as to steer the end effector and approach tissue.

Soft Suction-Based End Effector for Endoluminal Tissue Manipulation

This section addresses the design of an end effector for manipulation of endoluminal tissue. Millimeter-scale end effectors that provide safe and effective manipulation present a challenge for design and manufacturing. Previous work has primarily focused on jaw-like cable-actuated or shape-memory-alloy (SMA)-based grippers. Described herein is a soft suction-based gripper that can be integrated at the tip of an arm, as represented in FIG. 25.

Materials and Methods

The soft grippers are fabricated by molding DRAGON SKIN 20 platinum-cure silicone and ECOFLEX 0030 platinum-catalyzed silicone (both available from Smooth-On, Inc., of Macungie, PA, USA) using 3D-printed molds. Four grippers are fabricated for each material; the relevant dimensions are reported in the inset of FIG. 25. A variation on the design includes a 200-µm membrane fabricated by spin-coating ECOFLEX 0030 on a wafer at 800 revolutions per minute (rpm) for 30 seconds. The membrane is then bonded on the tip of the gripper to prevent clogging during suction.

The grippers are tested both in vitro and ex vivo. The in vitro characterization involved fixing the gripper on the moving tool of an INSTRON materials testing machine. Applying continuous vacuum pressure (−0.9 MPa relative to the atmospheric pressure) results in adhesion to the bottom plate. The maximum force before detachment is measured. In the ex-vivo test, pig stomach is selected as a specimen. The same protocol as was used for the in-vitro tests was adopted. The gripper was fixed in the same way; and the pig stomach was positioned on the bottom plate. In a final test, the gripper was used to tension the tissue specimen, and a scalpel was used to cut the specimen.

Results

Results from the in-vitro and ex-vivo tests were evaluated. In the in-vitro tests, the DS20 gripper was able to generate forces ranging from 0.9 to 1.26 N, while the ECOFLEX 0030 gripper provided roughly half this force. In the ex-vivo tests, the DRAGON SKIN 20 gripper was able to retract the tissue between 16 to 44 mm above the surface. The integration of the membrane leads to lower performance but still guarantees tissue tensioning and exposure for cutting (i.e., between 8 and 22 mm). The ECOFLEX 0030 gripper resulted in lower retraction both with and without the membrane.

Discussion

Introducing a soft suction-based gripper for endoluminal manipulation, two different materials were tested, one softer (ECOFLEX 0030 platinum-catalyzed silicone) and one stiffer (DRAGON SKIN 20 platinum-cure silicone). The first one provided low forces and thus lower tissue exposure, making it less suitable for effective tissue manipulation. The DRAGON SKIN 20 platinum-cure silicone showed promising performance, providing newton range forces in in-vitro conditions and tissue retraction up to 40 mm in ex-vivo conditions. The effect of integrating a membrane on the grippers to prevent clogging during operation was also investigated. The membrane reduces the performances of the gripper, although in the case of the DRAGON SKIN 20 gripper, it still provides a retraction of more than 10 mm. In order to better assess the functionality of the proposed gripper, a demonstration was performed showing that the provided tensioning is sufficient to enable cutting of the specimen using a scalpel that would reasonably need more force with respect to commonly used electrocautery devices. Since the gripper uses suction, it easily grasps the tissue as soon as the gripper is in contact with the tissue. In addition, due to its soft nature, the gripper passively follows changes in orientation during manipulation without requiring distal degrees of freedom (DoF).

Integration of the Soft Gripper on an Arm Extending from an Endoscope

In particular embodiments, an endoscope with a balloon-actuated arm extending from the distal end of the endoscope and including a soft gripper as an end effector can be passed through a human gastrointestinal conduit (e.g., the intestines). The soft gripper with a dome-shaped cup portion can be formed by casting or injection molding in, e.g., a 3D-printed mold. The soft gripper includes a central orifice in fluid communication with an external vacuum conduit coupled with a vacuum pump to generate a vacuum in the cup when the cup is placed on tissue, thereby securing the tissue to be retracted by the arm when the arm is displaced away from the tissue.

Laminate Soft Gripper

An illustration of a soft gripper device with an end effector 16 in the form of a laminate soft gripper structure is illustrated in FIGS. 26-29. The laminate soft gripper 16 is mounted to a decoupling structure (at its center), which, in turn, is mounted to a rigid plate 26 of a laminate linkage arm 14. Fluidic lines 24 for pumping fluid (gas or liquid) into the soft gripper 16 are defined on an internal surface of a silicone layer in the soft gripper 16. These channels 24 can be created, e.g., via soft lithography. In the soft lithography process, photolithography is used to fabricate a master, typically using a negative photoresist, such as SU-8 negative epoxy photoresist from MicroChem Corp. of Westborough, MA, US. The master is used as a mold on top of which soft materials are poured, and the soft materials will be embossed with the pattern defined by the exposed-and-developed photoresist and underlying mold. The patterned layer of elastomer is then bonded to another layer, typically using plasma treatment.

The resulting channels 24 can be used for pneumatic (or hydraulic) actuation to reshape the soft gripper 16 into a concave (dome) shape. The soft gripper 16 deforms as one side (i.e., the side closer to/facing the rigid plate 26) stretches (in-plane) more than the other, wherein the concavity will be established on the opposite (contacting) side of the soft gripper 16, which stretches less. Accordingly, the deformation of the soft gripper 16 can be directed away from the rigid plate 26 by using a softer material (with the embossed features for forming the channels 24) on the side of the laminate structure closer to the rigid plate 26 and a more-rigid layer on the contacting side of the soft gripper 16. The layer on the contacting side of the soft gripper 16 can also be made thicker than the layer on the other side of the channels 24 (closer to the rigid plate 26). Alternatively, the configuration of the layers can be reversed if a reduced pressure (vacuum) is applied to the internal channels 24 rather than pumping fluid into the channels 24; in such an embodiment, the size (e.g., diameter) of the channels 24 can be increased to amplify the collapsing of the soft gripper 16 due to the negative pressure. The soft grippers 16 can be mass produced from layered sheets, including silicone layers, aligned with alignment pins through the intersections of fixed markings on the sheets, bonded via plasma bonding, and then cut from the laminate along circular paths.

A step-wise method for forming a laminate linkage 14 is shown in FIG. 34 (with letters corresponding to the steps, below), wherein the steps of a fabrication of the multi-layer laminate linkage 14 are as follows:

A. Each soft layer is manufactured by pouring and spin coating silicone elastomers 70 on an SU-8-photoresist-patterned silicon wafer 72. Several soft layers can be manufactured with different embossed features using different wafers. Each has three alignment crosses to then refer each soft layer with the laser coordinate system.

B. The wafer 72 is put on top of a hot plate at 95° C. to cure the silicone elastomer 70 by thermal cross-linking.

C. The soft layer 70 is now formed, and it can be peeled off from the wafer 72 by making it adhere on a flexible layer 50 made with a polyimide (PI) film bonded on top of X8 WF double-sided adhesive gel film from Gel-Pak of Hayward, California, US.

D. The soft layer 70 is realigned with the laser coordinate system by exploiting the three alignment crosses, and the soft layer 70 is laser cut. Alignment holes are cut through the soft layer 70, and the flexible layer 50 and additional patterns are cut only onto the soft layer 70 to remove the silicone elastomer in specific locations (if necessary).

E. Two soft layers 70 (fabricated as explained in steps 1-4, above) are treated with oxygen plasma in order to make their surface hydrophilic via OH— surface groups.

F. The layers 70 and 50 are realigned using the alignment holes (machined in step 4) on top of an alignment jig and bonded.

G. To complete the bonding process, one waits a few minutes.

H. The two bonded layers 70 and 50 are removed from the alignment jig, and the flexible support 50 (polyimide film bonded on top of the X8 WF adhesive gel film from Gel-Pak) is removed from the top soft layer 70. At this point, it is possible to reiterate from step 5 and bond other soft layers 70 on top.

I. Rigid layers (plates) 26 are laser machined.

J. The rigid layers 26 are chemically modified with $O_2$ plasma.

K. The rigid layers 26 are chemically modified with APTES.

L. The chemically modified rigid layers 26 and $O_2$-plasma-treated soft layers 70 are realigned using dowels on an alignment jig.

M. The chemically modified rigid layers 26 are bonded to the soft layers 70.

N. The resulting hard/soft layer 26/70 is removed from the alignment jig, and the flexible support 50 is removed from the top of the stack.

O. The full stack (with the following sequence of layers from top to bottom: rigid layer 26, biocompatible adhesive 74, flexure layer 50, adhesive 74, soft layer 70, rigid layer 26, biocompatible adhesive 74, flexure layer 50, biocompatible adhesive 74, and rigid layer 26) is placed on an alignment jig and laminated.

P. The laminated stack is removed from the alignment jig and laser-machined to produce release cuts in the laminate.

Q. The final soft pop-up laminate linkages 14 are released from the surrounding substrate The above method, obviates the need for manual cutting and assembling of soft components, thus providing for a more accurate and faster fabrication of the actuators.

Soft Gripper Device Including Arm

The laminate linkage arms 14, discussed above, can be similarly fabricated via a mass laminate fabrication technique, likewise using alignment crosses and pins, plasma bonding and laser cutting along the green paths. Fluidic channels 14 are provided on an interior surface of at least one of the layers (e.g., a layer formed of a silicone, such as a polydimethylsiloxane layer) to provide respective pathways for (a) generating a reduced pressure to create a vacuum effect by removing gas through the center of the soft gripper 16 and (b) pumping fluid into interior channels 14 of the soft gripper 16 to curl the planar soft gripper 16 into a dome shape, as shown in FIG. 31.

Illustrations of the layers and steps in a fabrication process for producing a laminate soft gripper device are provided in FIGS. 35-37, wherein the fabrication of four layers (each in its own row) of the laminate structure is illustrated. Each layer begins with a wafer substrate 72 upon which the silicone elastomer 70 or other polymer is coated. The wafers 72 used for layers 2 and 4 also include surface features for forming the fluidic lines 24 through the rigid plate 26 and through the soft gripper 15. After the polymer layers 70 are peeled off the wafers 72, the shapes for the respective parts of the device can be laser cut from the polymer sheets.

Figure 29:

Perspective, top, bottom and sectional views of a semi-transparent soft gripper device with a laminate soft gripper, as described above, are provided in FIGS. 26-29. The internal radiating channels 24 for deforming the soft gripper 16 via pneumatics or hydraulics can be particularly seen in FIGS. 28 and 29; and the central orifice 78 in the soft gripper 16 through which the vacuum is drawn can be particularly seen at bottom center in the soft gripper 16, as depicted in the sectional view of FIG. 29. The laminate soft gripper 16 is flat (with a substantially planar contacting surface), as shown in FIG. 29, and it can be mounted (flat) at the distal end of a laminate linkage arm 14 attached to an endoscope 12, as shown in FIG. 25. The soft gripper 16 can have a thickness (measure vertically in the orientation of FIG. 29) of about 5 mm.

The interconnected fluidic lines 24 and other channels in the arm 14 and in the soft gripper 16 can be formed by channels defined on a surface of one or more layers of the laminate structure. Hence, no external conduits are needed for pumping the fluids into and through the soft actuator 16 in these embodiments.

Additional views of a laminate embodiment of a soft gripper, with external conduits in this case, are provided with the soft gripper in a flat, unactuated configuration (FIG. 30) and in an actuated dome shape formed by pumping fluid (e.g., increasing the pressure) in the internal channels of the soft gripper (FIG. 31.

After making contact with a surface, the soft gripper is pneumatically (or hydraulically) actuated by pumping fluid into the internal channels to create the dome shape, as shown in FIG. 32; and a suction is then generated through the central orifice of the soft gripper to adhere the soft gripper via suction to the surface so that the objected to which the soft gripper is attached can then be displaced (or held in place), as shown in FIG. 33.

Additional examples consistent with the present teachings are set out in the following numbered clauses:

1. A laminate linkage with soft actuation, comprising:
   a plurality of rigid plates joined at flexible joints;
   at least one balloon bonded to at least one of the rigid plates and configured to generate a displacement of at least one of the rigid plates selected from extension, a change of yaw, a change of pitch, and combinations thereof; and
   a fluid source in fluid communication with an interior volume of the balloon and configured to pump fluid into the balloon to generate the displacement of at least one of the rigid plates.
2. The laminate linkage of clause 1, comprising a plurality of the balloons, respectively joined to different rigid plates.
3. The laminate linkage of clause 2, wherein different balloons are configured to generate different types of displacement.
4. The laminate linkage of clause 3, wherein respective balloons are configured to respectively generate extension, the change of yaw, and the change of pitch of rigid plates.
5. The laminate linkage of any of clauses 1-4, wherein the balloons and rigid plates are laminated together.
6. The laminate linkage of clause 5, wherein the lamination is achieved via a technique selected from ultrasonic bonding, plasma bonding, adhesive bonding, and thermoforming.
7. The laminate linkage of any of clauses 1-6, wherein the laminate linkage is mounted on a flexible instrument.
8. The laminate linkage of clause 7, wherein the flexible instrument is an endoscope.
9. The laminate linkage of any of clauses 1-8, wherein the rigid plates and balloons are optically transparent.
10. The laminate linkage of any of clauses 1-9, wherein the balloons comprise a mixture of silicone elastomers across a range of hardnesses or elastic moduli.
11. The laminate linkage of any of clauses 1-10, wherein at least one of the balloons is mounted external to a joint between rigid plates.
12. The laminate linkage of any of clauses 1-11, wherein at least one of the balloons is mounted internal to a joint between rigid plates.
13. The laminate linkage of any of clauses 1-12, further comprising sensors mounted along the linkage to detect contact forces or for positioning.
14. The laminate linkage of any of clauses 1-13, where the dimensions of the laminate linkage range from 1-5 mm.
15. The laminate linkage of any of clauses 1-14, further comprising a soft gripper mounted at a distal end of the laminate linkage.
16. The laminate linkage of clause 15, wherein the soft gripper is suction-based.
17. The laminate linkage of clause 15 or 16, wherein the soft gripper comprises a soft polymer, and wherein the soft gripper defines a central orifice providing a fluid passage way through the soft gripper.
18. The laminate linkage of any of clauses 15-17, wherein the soft gripper has a multi-layer laminate structure.
19. The laminate linkage of clause 18, further comprising a pneumatic or hydraulic actuator, wherein at least one of the layers of the laminate structure includes an interior surface that defines grooves extending away from the central orifice, wherein the grooves define internal channels in combination with an adjoining layer, and wherein the internal channels are in fluid communication with the pneumatic or hydraulic actuator such that fluid can be pumped into the channels to deform the soft gripper into a dome shape.
20. The laminate linkage of clause 19, wherein the laminate structure further defines conduits that (a) provide the fluid communication between the central orifice and the vacuum source and (b) provide the fluid communication between the internal channels and the pneumatic or hydraulic actuator.
21. The laminate linkage of any of clauses 1-20, wherein outer surfaces of the laminate linkage are all formed of biocompatible material.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step.

Likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions, and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims (or where methods are elsewhere recited), where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A laminate linkage with soft actuation, comprising: a plurality of rigid plates connected in series and joined at flexible joints; at least one balloon bonded to at least one of the rigid plates and configured to generate a plurality of displacements in series about or across distinct orientations, wherein the displacements are to a plurality of the rigid plates, and wherein the displacements are selected from a plurality of the following: extension, a change of yaw, a change of pitch, and combinations thereof; a pair of rigid plates connected via flexible joints in parallel to form a Sarrus linkage; an additional balloon embedded between the rigid plates connected in parallel and configured to actuate the Sarrus linkage; and a fluid source in fluid communication with an interior volume of the at least one balloon and of the additional balloon and configured to pump fluid into the at least one balloon to generate the series of displacements of the rigid plates and into the additional balloon to actuate the Sarrus linkage.

2. The laminate linkage of claim 1, wherein the balloons and rigid plates are laminated together.

3. The laminate linkage of claim 2, wherein the lamination is achieved via a technique selected from ultrasonic bonding, plasma bonding, adhesive bonding, and thermoforming.

4. The laminate linkage of claim 1, wherein the laminate linkage is mounted on a flexible instrument.

5. The laminate linkage of claim 4, wherein the flexible instrument is an endoscope.

6. The laminate linkage of claim 1, wherein the rigid plates and the balloons are optically transparent.

7. The laminate linkage of claim 1, further comprising at least one sensor mounted along the laminate linkage to detect contact forces or for positioning.

8. The laminate linkage of claim 1, where the dimensions of the laminate linkage range from 1-5 mm.

9. The laminate linkage of claim 1, further comprising a soft gripper mounted at a distal end of the laminate linkage.

10. The laminate linkage of claim 1, wherein outer surfaces of the laminate linkage are all formed of biocompatible material.

* * * * *